US010662136B2

(12) United States Patent
Clark et al.

(10) Patent No.: US 10,662,136 B2
(45) Date of Patent: *May 26, 2020

(54) PROCESS OF SEPARATING COMPONENTS OF A FERMENTATION BROTH

(71) Applicant: Genomatica, Inc., San Diego, CA (US)

(72) Inventors: Warren Clark, Yale, OK (US); Michael Japs, San Diego, CA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/975,630

(22) Filed: May 9, 2018

(65) Prior Publication Data
US 2019/0112247 A1 Apr. 18, 2019

Related U.S. Application Data

(63) Continuation of application No. 14/066,598, filed on Oct. 29, 2013, now Pat. No. 9,994,505, which is a continuation of application No. 12/793,623, filed on Jun. 3, 2010, now Pat. No. 8,597,918.

(60) Provisional application No. 61/184,292, filed on Jun. 4, 2009.

(51) Int. Cl.
C07C 29/76 (2006.01)
C12P 7/18 (2006.01)

(52) U.S. Cl.
CPC .............. *C07C 29/76* (2013.01); *C12P 7/18* (2013.01)

(58) Field of Classification Search
None
See application file for complete search history.

(56) References Cited

U.S. PATENT DOCUMENTS

| | | | |
|---|---|---|---|
| 3,175,962 A | 3/1965 | Holtslag | |
| 3,976,430 A | 8/1976 | Houston et al. | |
| 5,209,825 A | 5/1993 | Badat et al. | |
| 5,342,488 A | 8/1994 | Gosch et al. | |
| 5,608,146 A | 3/1997 | Frommer et al. | |
| 5,766,439 A | 6/1998 | Eyal et al. | |
| 5,772,890 A | 6/1998 | Hubred | |
| 5,981,810 A | 11/1999 | Okuyama et al. | |
| 5,986,133 A | 11/1999 | Holtzapple et al. | |
| 6,228,579 B1 | 5/2001 | Zyskind et al. | |
| 6,361,983 B1 | 3/2002 | Ames | |
| 6,515,187 B1 | 2/2003 | Schon et al. | |
| 6,821,396 B2 | 11/2004 | Wolfert et al. | |
| 6,846,389 B2 | 1/2005 | Kaibel et al. | |
| 6,913,674 B2 | 7/2005 | Wolfert et al. | |
| 6,986,833 B2 | 7/2006 | Wolfert et al. | |
| 7,708,865 B2 | 5/2010 | Holtzapple et al. | |
| 7,858,350 B2 | 12/2010 | Burk et al. | |
| 7,893,305 B2 | 2/2011 | Liu et al. | |
| 7,919,658 B2 | 4/2011 | Adkesson et al. | |
| 7,947,483 B2 | 5/2011 | Burgard et al. | |
| 7,985,566 B2 | 7/2011 | Aoshima et al. | |
| 8,021,864 B2 | 9/2011 | Aoshima et al. | |
| 8,048,661 B2 | 11/2011 | Burgard et al. | |
| 8,067,214 B2 * | 11/2011 | Burk | C12N 9/0006 435/158 |
| 8,129,156 B2 | 3/2012 | Burk et al. | |
| 8,129,169 B2 | 3/2012 | Van Dien et al. | |
| 8,178,327 B2 | 5/2012 | Burk et al. | |
| 8,183,417 B2 | 5/2012 | Adkesson et al. | |
| 8,357,520 B2 | 1/2013 | Burk et al. | |
| 8,377,666 B2 | 2/2013 | Haselbeck et al. | |
| 8,377,667 B2 | 2/2013 | Haselbeck et al. | |
| 8,445,244 B2 | 5/2013 | Burgard et al. | |
| 8,470,582 B2 | 6/2013 | Burgard et al. | |
| 8,530,210 B2 | 9/2013 | Sun et al. | |
| 8,597,918 B2 | 12/2013 | Clark et al. | |
| 9,018,424 B2 | 4/2015 | Morita et al. | |
| 2003/0106786 A1 | 6/2003 | Kaibel et al. | |
| 2003/0203459 A1 | 10/2003 | Chen et al. | |
| 2003/0233218 A1 | 12/2003 | Schilling | |

(Continued)

FOREIGN PATENT DOCUMENTS

DE 102005042541 3/2007
EP 1882712 1/2008

(Continued)

OTHER PUBLICATIONS

Pierrot P et al. Continuous Acetone-Butanol Fermentation with High Productivity by Cell Ultrafiltration and Recycling. 1986. Biotechnology Letters. vol. 8, No. 4. 253-256. (Year: 1986).*

"DSM approves BDO made using Genomatica's process for use in Arnitel products," Press release dated Oct. 8, 2013, Singapore (2 pages).

"Genomatica delivers on plant performance guarantees," Genomatica press release dated Jun. 28, 2017 (3 pages).

Ahmed and Lewis, "Fermentation of biomass-generated synthesis gas: effects of nitric oxide," Biotechnol. Bioeng. (2007), vol. 97, pp. 1080-1086.

Atsumi et al., "Non-fermentative pathways for synthesis of branched-chain higher alcohols as biofuels," Nature (2008), vol. 451, Issue 7174, pp. 86-89.

(Continued)

*Primary Examiner* — Paul J Holland
(74) *Attorney, Agent, or Firm* — Jones Day

(57) ABSTRACT

A process of isolating 1,4-butanediol (1,4-BDO) from a fermentation broth includes separating a liquid fraction enriched in 1,4-BDO from a solid fraction comprising cells, removing water from said liquid fraction, removing salts from said liquid fraction, and purifying 1,4-BDO. A process for producing 1,4-BDO includes culturing a 1,4-BDO-producing microorganism in a fermentor for a sufficient period of time to produce 1,4-BDO. The 1,4-BDO-producing microorganism includes a microorganism having a 1,4-BDO pathway having one or more exogenous genes encoding a 1,4-BDO pathway enzyme and/or one or more gene disruptions. The process for producing 1,4-BDO further includes isolating 1,4-BDO.

14 Claims, 16 Drawing Sheets

(56) References Cited

U.S. PATENT DOCUMENTS

| | | |
|---|---|---|
| 2005/0069997 A1 | 3/2005 | Adkesson et al. |
| 2005/0221466 A1 | 10/2005 | Liao et al. |
| 2006/0041152 A1 | 2/2006 | Cantrell et al. |
| 2009/0023182 A1 | 1/2009 | Schilling |
| 2009/0047719 A1 | 2/2009 | Burgard et al. |
| 2009/0075351 A1 | 3/2009 | Burk et al. |
| 2009/0275096 A1 | 11/2009 | Burgard et al. |
| 2010/0101931 A1 | 4/2010 | Pinkos et al. |
| 2010/0317902 A1 | 12/2010 | Liu et al. |
| 2010/0330634 A1 | 12/2010 | Park et al. |
| 2011/0003355 A1 | 1/2011 | Clark et al. |
| 2011/0014669 A1 | 1/2011 | Madden et al. |
| 2011/0129904 A1 | 6/2011 | Burgard et al. |
| 2011/0201068 A1 | 8/2011 | Pharkya et al. |
| 2011/0212507 A1 | 9/2011 | Burgard et al. |
| 2012/0094345 A1 | 4/2012 | Burk et al. |
| 2012/0225463 A1 | 9/2012 | Van Dien et al. |
| 2013/0196397 A1 | 8/2013 | Burk et al. |
| 2014/0275465 A1 | 9/2014 | Garikipati et al. |
| 2015/0087038 A1 | 3/2015 | Utsunomiya et al. |

FOREIGN PATENT DOCUMENTS

| | | | |
|---|---|---|---|
| EP | 2355911 | 8/2011 | |
| JP | A-S62-285779 | 4/1986 | |
| JP | A S61 254177 | 11/1986 | |
| JP | A H05 201899 | 8/1993 | |
| JP | A 2003 511360 | 3/2003 | |
| JP | A 2004 524852 | 8/2004 | |
| JP | A 2008 212156 | 9/2008 | |
| JP | A 2008 245537 | 10/2008 | |
| WO | WO 2001/085708 | 11/2001 | |
| WO | WO 2002/086135 | 10/2002 | |
| WO | WO-02086135 A2 * | 10/2002 | ......... B01D 15/1814 |
| WO | WO 2004/015145 | 2/2004 | |
| WO | WO 2004/101479 | 11/2004 | |
| WO | WO-2004101479 A2 * | 11/2004 | ........... B01D 61/027 |
| WO | WO 2007/030830 | 3/2007 | |
| WO | WO 2008/098621 | 8/2008 | |
| WO | WO 2008/098622 | 8/2008 | |
| WO | WO 2008/115840 | 9/2008 | |
| WO | WO 2009/023493 | 2/2009 | |
| WO | WO 2009/047275 | 4/2009 | |
| WO | WO 2009/094485 | 7/2009 | |
| WO | WO 2010/006076 | 1/2010 | |
| WO | WO 2010/085731 | 7/2010 | |
| WO | WO 2010/037843 | 8/2010 | |
| WO | WO 2011/123270 | 6/2011 | |
| WO | WO 2011/123269 | 10/2011 | |
| WO | WO 2011/137192 | 11/2011 | |
| WO | WO 2012/158180 | 11/2012 | |
| WO | WO 2014/170759 | 10/2014 | |

OTHER PUBLICATIONS

Chlup et al., "Disc stack centrifuge operating parameters and their impact on yeast physiology," J. Inst. Brewing, 114(1):45-61 (2008).
Cukalovic et al., "Feasibility of production method for succinic acid derivatives: a marriage of renewable resources and chemical technology," Biofuels Bioprod. Bioref. (2008), vol. 2, pp. 505-529.
Datar et al., "Fermentation of biomass-generated producer gas to ethanol," Biotechnol. Bioeng, (2004), vol. 86, pp. 587-594.
Durre et al., "Microbial Production of Acetone/Butanol/Isopropanol," In Biotechnology, vol. 6: "Products of Primary Metabolism", Second edition, M. Roehr, ed. Published jointly by: VCH Verlagsgesellschaft mbH, Weinheim, Federal Republic of Germany and VCH Publishers Inc., New York, NY (1996). pp. 229-268.
European Patent Office, "Supplementary European Search Report for European Patent Application No. EP10784131," (dated Sep. 13, 2013).
Forster et al., "Genome-scale reconstruction of the *Saccharomyces cerevisiae* metabolic network," Genome Res. (2003), vol. 13, pp. 244-253.

Gerhardt et al., "Fermentation of 4-aminobutyrate by Clostridium aminobutyricum: cloning of two genes involved in the formation and dehydration of 4-hydroxybutyryi-CoA," Arch. Microbial., (2000), vol. 174, pp. 189-199.
Gong et al., "Effects of transport properites of ion-exchange membranes on desalination of 1,3-propanediol fermentation broth by electrodialysis," Desalination, (2006), vol. 191, pp. 193-199.
Hanai et al., "Engineered synthetic pathway for isopropanol production in *Escherichia coli*," Appl. Environ. Microbial. (2007), vol. 73, pp. 7814-7818.
Hein et al., "Biosynthesis of poly(4-hydroxybutyric acid) by recombinant strains of *Escherichia coli*," FEMS Microbial., Lett., (1997), vol. 153, Issue 2, pp. 411-418.
Ichikawa et al. "Catalytic reaction of 1,3-butanediol over solid acids," J. Mol. Catalysis A Chem., (2006), vol. 256, pp. 106-112.
Ichikawa et al., "PIO study on 1,3-butanediol dehydration over Ce02 (1 1 1) surface," J. Mol. Catalvsis A Chem., (2005), vol. 231, pp. 181-189.
International Searching Authority, "International Search Report and Written Opinion for PCT/US2010/037329," (dated Aug. 30, 2010).
Jojima et al., "Production of isopropanol by metabolically engineered *Escherichia coli*," Appl. Microbiol. Biotechnol., (2008), vol. 77, pp. 1219-1224.
Jones and Woods, "Acetone-butanol fermentation revisited," Microbial. Rev., (1986), vol. 50, Issue 4, pp. 484-524.
Kato et al., "Production of a novel copolyester of 3-hydroxybutyric acid with a medium-chain-length 3-hydroxyalkanoic acids by *Pseudomonas* sp. 61-3 from sugars," Appl. Microbial. Biotechnol., (1996), vol. 45, pp. 363-370.
Kim et al., "Construction of an *Escherichia coli* K-12 mutant for homoethanologenic fermentation of glucose or xylose without foreign genes," Appl. Environ. Microbial., (2007), vol. 73, pp. 1766-1771.
Kobayashi et al., "Fermentative Production of 1,4-Butanediol from Sugars by *Bacillus* sp.," Agric. Biol. Chem., (1987), vol. 51, Issue 6, pp. 1689-1690.
Lee et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp. A33," Appl. Microbial. Biotechnol., (1995), vol. 42, pp. 901-909.
Lee et al., "Biosynthesis of enantiopure (s)-3-hydroxybutyric acid in metabolically engineered *Escherichia coli*," Appl. Microbial. Biotechnol., (2008), vol. 79, Issue 4, pp. 633-641.
Lee et al., "Natural organic matter (NOM) fouling in low pressure membrane filtration—effect of membranes and operation modes," Desalination, 218:257-270 (2008).
Lehman et al., "Application of ceramic membranes with pre-ozonation for treatment of secondary wastewater effluent," Water Research, 43:2020-2028 (2009).
Lin et al., "Fed-batch culture of a metabolically engineered *Escherichia coli* strain designed for high-level succinate production and yield under aerobic conditions," Biotechnol. Bioeng., (2005), vol. 90, Issue 6, pp. 775-779.
Mahadevan and Schilling, "The effects of alternate optimal solutions in constraint based genome-scale metabolic models," Metab. Eng., (2003), vol. 5, Issue 4, pp. 264-276.
Mahadevan et al., "Application of metabolic modeling to drive bioprocess development for the production of value-added chemicals," Biotechnol. Bioprocess Eng., (2005), vol. 10, Issue 5, pp. 408-417.
Nakano et al., "Characterization of Anaerobic Fermentative Growth of Bacillus subtilis: Identification of Fermentation End Products and Genes Required for Growth," J. Bacterial., (1997), vol. 179, Issue 21, pp. 6749-6755.
Nexant, "1,4-Butanediol/THF—PERP Program New Report Alert," Nexant ChemSystems PERP Report 02/03-7, (Jan. 2004), pp. 1-5.
Park et al., "Biosynthesis of poly(3-hydroxybutyrate-co-3-hydroxyalkanoates) by metabolically engineered *Escherichia coli* strains," Appl. Biochem. Biotechnol. (2004), vol. 113-116, pp. 335-346.
Pierrot et al., "Continous Acetone-Butanol Fermentation with High Productivity by Cell Ultrafiltrarion and Recycling," Bitechnology Letters, 8(4):253-256 (1986).

(56) References Cited

OTHER PUBLICATIONS

Safe Drinking Water Formulation, www.safewater.org, pp. 1-16 (2007).
Schaep, J., "Modelling the retention of ionic components for different nanofiltration membranes," Separation and Purification Technology, (2001), pp. 22-23 and 169-179.
Schilling et al., "Combining Pathway Analysis with Flux Balance Analysis for the Comprehensive Study of Metabolic Systems," Biotechnol. Bioeng., (2000-2001), vol. 71, Issue 4, pp. 286-306.
Schilling et al., "Theory for the Systematic Definition of Metabolic Pathways and Their Use in Interpreting Metabolic Function from a Pathway-Oriented Perspective," J. Theor. Biol., (2000), vol. 203, Issue 3, pp. 229-248.
Schilling et al., "Toward Metabolic Phenomics: Analysis of Genomic Data Using Flux Balances," Biotechnol. Proa., (1999), vol. 15, pp. 288-295.
Werpy et al., "Top Value Added Chemicals from Biomass. Volume I-Results of Screening for Potential Candidates from Sugars and Synthesis Gas," (2004), DOE Report.
Yavorsky, D., et al., "The clarification of bioreactor cell cultures for biopharmaceuticals," Pharmacology Technology (2003), pp. 62-76.

\* cited by examiner

1. Calandria
2. Separator
3. Condensor

PROCESS OF SEPARATING COMPONENTS OF A FERMENTATION BROTH This application is a continuation under 35 U.S.C. § 120 of U.S. patent application Ser. No. 14/066,598, filed Oct. 29, 2013, now U.S. Pat. No. 9,994,505, which is a continuation under 35 U.S.C. § 120 of U.S. patent application Ser. No. 12/793,623, filed Jun. 3, 2010, now U.S. Pat. No. 8,597,918, which claims the benefit of priority of U.S. Provisional Application Ser. No. 61/184,292, filed Jun. 4, 2009, the entire contents of each of which are incorporated herein by reference.

BACKGROUND OF THE INVENTION

This invention relates generally to the separation of components of a fermentation broth and, more specifically to the isolation of water miscible compounds having boiling points higher than water from other fermentation broth components.

Environmental and cost reduction incentives exist to design process schemes that have the ability to separate and optionally recycle components in a fermentation including the cell mass, residual media and media salts, residual substrate such as sucrose and/or glucose, and water. Efforts have also been made to recycle cell mass as a means to improve the fermentation productivity. Less effort has been made in the area of recovering the residual media and media salts for reuse in the fermentation. In this regard, most efforts have focused on reducing initial media costs, rather than downstream recovery. The resulting "low cost" media is often not optimal for cell growth and product production. By developing effective methods for the recovery of media components, a more optimal media recipe can be utilized with fewer restrictions on initial raw material costs.

The isolation of compounds on large scale with useful purity is a complex challenge in process chemistry. Differences in scale alone can render isolation procedures developed on laboratory benchtop scale impractical or even not viable at pilot or commercial scales. Isolation of compounds from complex mixtures depends on numerous factors including whether the compound is a solid or liquid at ambient temperatures, the compounds boiling point, density, polarity, the presence or absence of pH sensitive functional groups, and solubility in organic solvents versus water. These factors also apply to all other components of the mixture from which the compound of interest is to be isolated. Another property that factors into isolation of a compound, organic compounds in particular, is how it partitions between two immiscible phases, such as between water and an organic solvent. Compounds that are particularly polar are often more soluble in water than in common organic solvents used in extraction processes. Some compounds are particularly challenging to isolate from water by extractive methods due to their amphiphilic character. Amphiphiles are compounds that possess both a polar portion and a lipophilic portion. These compounds can complicate isolation by extraction by causing intractable emulsions.

Moreover, when a compound is prepared from a fermentation the amount of water can be substantially higher than the compound of interest, requiring isolation of a minor component from a complex mixture. Isolation of compounds that boil at a higher temperature than water further adds to the complexity and cost of the separation since the compound cannot be distilled directly from the fermentation broth as is the case, for example, in an ethanol fermentation process. In this regard, interactions between the compound of interest and water can cause the two entities to co-distill as an azeotrope at a boiling point different from the two purified components. Azeotrope formation is not readily predictable. This can diminish recovery of the compound of interest when trying to separate it from water. When a compound has polar functional groups another concern is how it may interact with other compounds present in the water phase, including any salts and metal ions, for example.

The nature of the functional groups present in a compound of interest can complicate the separation of salts. For example, one or more functional groups of a compound can interact with or chelate cations or anions. Chelation occurs in a size dependent manner with respect to the cation or anion and is also dependent on the disposition of the functional groups on the compound of interest. Chelation and other interactions can render some salts soluble in a liquid compound even in the absence of water, while other salts can be insoluble in the absence of water despite the presence of a compound with functional groups capable of interacting with salts. These types of effects on salt solubility are difficult to predict. Further adding to the complexity of the interaction between a compound and salts, is the nature of any co-solvents. For example, during the isolation of a compound of interest that is water miscible, hydrogen bonding and other interactions with water can disrupt the interaction between the salts and the compound of interest. Thus, in some cases a salt can be separated more readily from a compound in the presence of some amount of water. However, the amount of water that balances salt supersaturation allowing salt separation by crystallization, for example, while maintaining water's ability to disrupt chelation and other interactions between a compound of interest and any salts is difficult to predict.

Yet a further challenge in developing isolation methods is the potential reactivity of biosynthetic byproducts such as organic acids, excess substrate, and the like. Under conditions of heating, excess substrate can degrade and cause undesirable coloration of product. Additionally, some byproducts can react with the product of interest, effectively lowering isolation yields. These byproducts can include those formed during fermentation as well as byproducts formed during steps of the isolation procedure itself, for example due to degradation processes at elevated temperatures during a distillation, water evaporation, and the like.

Thus, there is a need to develop processes that allow for the isolation of water miscible compounds that have boiling points higher than water from microbial fermentations, while bearing in mind the environmental and cost benefit of recycling other fermentation components. The present invention satisfies this need and provides related advantages as well.

SUMMARY OF THE INVENTION

In some aspects, embodiments disclosed herein relate to process of isolating 1,4-butanediol (1,4-BDO) from a fermentation broth that includes separating a liquid fraction enriched in 1,4-BDO from a solid fraction comprising cells, removing water from said liquid fraction, removing salts from said liquid fraction, and purifying 1,4-BDO.

In other aspects, embodiments disclosed herein relate to a process of isolating 1,4-BDO from a fermentation broth that includes removing a portion of solids by disc stack centrifugation to provide a liquid fraction, removing a further portion of solids from the liquid fraction by ultrafiltration, removing a portion of salts from the liquid fraction by evaporative crystallization, removing a further portion of salts from the liquid fraction by ion exchange, and distilling 1,4-BDO.

In still other aspects, embodiments disclosed herein relate to a process of isolating 1,4-BDO from a fermentation broth that includes removing a portion of solids by disc stack centrifugation to provide a liquid fraction, removing a further portion of solids from the liquid fraction by ultrafiltration, removing a portion of salts from the liquid fraction by nanofiltration, removing a further portion of salts from the liquid fraction by ion exchange, evaporating a portion of water, and distilling 1,4-BDO.

In yet still other aspects, embodiments disclosed herein relate to a process for producing 1,4-BDO that includes culturing a 1,4-BDO-producing microorganism in a fermentor for a sufficient period of time to produce 1,4-BDO. The 1,4-BDO-producing microorganism includes a microorganism having a 1,4-BDO pathway including one or more exogenous genes encoding a 1,4-BDO pathway enzyme and/or one or more gene disruptions. The process further includes isolating 1,4-BDO according to the described isolation processes.

DETAILED DESCRIPTION OF THE INVENTION

Figure 1:
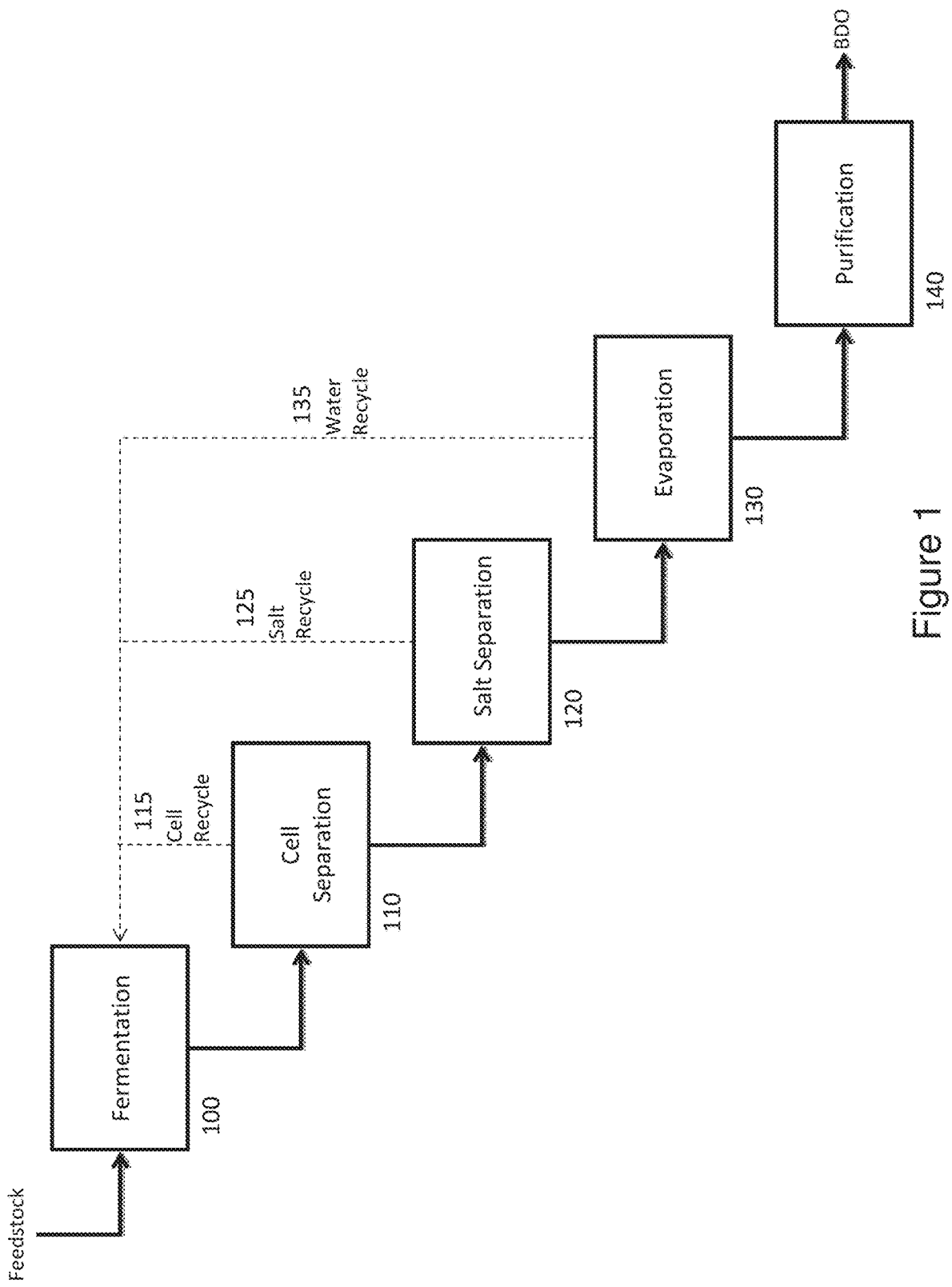
FIG. 1 shows a block diagram of steps in the process of purifying 1,4-BDO from a fermentation broth.

Fermentation production of commodity chemicals is a useful alternative to traditional production using nonrenewable fossil fuel feedstocks. With the ability to utilize renewable feedstocks such as recycled biomass and the like, the process can prove more economical and environmentally sound than fossil fuel based production. Products generated from fermentation can be useful in many applications. In specific embodiments, the present invention provides methods for the production of 1,4-BDO. 1,4-Butanediol (BDO) is a polymer intermediate and industrial solvent. Downstream, butanediol can be further transformed; for example, by oxidation to gamma-butyrolactone, which can be further converted to pyrrolidone and N-methyl-pyrrolidone, or it can undergo hydrogenolysis to tetrahydrofuran. These compounds have varied uses as polymer intermediates, solvents, and additives.

This invention is directed, in part, to processes for isolating water miscible compounds having boiling points higher than water from a fermentation while optionally allowing recycle of other components of the fermentation broth. The process separates out cell mass, which can include microbial organisms that have been engineered with gene insertions, gene disruptions or a combination of insertions and disruptions to produce compounds in useful yields from a suitable feedstock.

The cell-free broth, or liquid fraction, can be further processed by removal of salts. This can be achieved by several methods before or after removal of some or substantially all of the water from the fermentation broth. As described above, salts are not often recovered for recycle in a fermentation process. Usually any salt recovery involves a salt form of a desired biosynthetic product such as lactate, citrate or other carboxylate product or ammonium salts of amine-containing products, rather than media salts and the like. The process described herein allows for recovery of media salts and optional recycle back into fermentation. The isolation process also involves removal of water, which can be reintroduced into the fermentation system. In the final purification, the compound produced by fermentation can be distilled, or recrystallized if solid, from the remaining liquid fraction after removal of cells, salts, and water. In the case of a liquid, the final purification can be accomplished by fractional distillation, for example.

In some embodiments, the invention is directed to a process of isolating a water miscible compound of interest having a boiling point higher than water from a fermentation broth. The process includes (1) separating a liquid fraction enriched in the compound from a solid fraction that includes cells; (2) removing water from the liquid fraction; (3) removing salts from the liquid fraction, and (4) purifying the compound of interest by distillation or recrystallization. Steps (2) and (3) above may be performed in either order, or together.

Compounds of interest with boiling points higher than water that are accessible via fermentation, can have boiling points 10° C., 20° C., 30° C., 40° C., 50° C., 60° C., 70° C., 80° C., 90° C., 100° C., 150° C., 200° C. and 300° C. higher than water and more, including all values in between. Compounds of interest having higher boiling points than water can include, for example, 1,4-BDO, 1,3-BDO, 2,3-BDO, 1,3-PDO, 1,2-PDO (methyl ethyl glycol), 1,2-ethandiol (ethylene glycol), gamma-butyrolactone (GBL), 1,5-pentanediol, 1,6-hexanediol. Furthermore, compounds of interest include those that are water miscible. In some embodiments, such water miscible compounds can be recalcitrant to conventional extraction procedures. Additionally, compounds of interest include those that are neutral. As used herein, a neutral compound refers to a compound that does not possess functional groups capable of carrying charge, such as amines, carboxylic acids, sulfonic acids, boronic acids and the like. Finally, compounds of interest can be sufficiently small so as to be permeable to a nanofiltration membrane, as described further below. Exemplary compound classes include alcohols, diols, triols, such as glycerin, tetraols, polyols and the like.

In one specific embodiment, the compound of interest is 1,4-BDO. 1,4-BDO has a boiling point of about 230° C. and is completely miscible with water. Moreover, there are no solvents that have been identified that can economically extract 1,4-BDO from the water. As a neutral molecule, isolation by crystallization of a salt form is precluded. 1,4-BDO has a molecular weight sufficiently low to pass through a nanofiltration membrane as described in Example III below. Furthermore, the solubility of various fermentation media salts in pure 1,4-BDO is relatively low, as described in Example VI below.

In some embodiments, the present invention provides a process of isolating 1,4-butanediol (1,4-BDO) from a fermentation broth that includes (1) separating a liquid fraction enriched in 1,4-BDO from a solid fraction that includes cells; (2) removing water from the liquid fraction; (3) removing salts from the liquid fraction, and (4) purifying 1,4-BDO.

One skilled in the art will recognize that given the guidance of the teachings disclosed herein with respect to the exemplary compound 1,4-BDO, other water miscible compounds of interest having boiling points higher than water can be isolated using the same procedures. For example, the methods disclosed herein are readily modified to enable the isolation of 1,3-butanediol. Therefore, although many embodiments are exemplified by 1,4-BDO, it is understood that the methods are readily adaptable to other water miscible compounds of interest having boiling points higher than water.

In some embodiments, the invention is directed to a process of isolating 1,4-butanediol (1,4-BDO) from a fermentation broth. The process includes separating a liquid fraction enriched in 1,4-BDO from a solid fraction that includes cells. Water is evaporated from the liquid fraction before or after separating salts from the liquid fraction. In some embodiments 1,4-BDO is separated from salts that have crystallized after water removal as described further below. The salts have a low solubility in 1,4-BDO such that the separated 1,4-BDO is about 98% salt-free. In some embodiments, salts are separated by special filtration methods and/or ion exchange, or chromatographic methods prior to water removal as described further below.

As used herein, "isolating" refers to a process that includes purification steps to obtain a substantially purified compound of interest. In particular embodiments, a compound of interest includes 1,4-BDO. A substantially purified compound includes those that are at least 98% salt free, in some embodiments, at least 99% salt free in other embodiments, and at least 99.5% salt free in still other embodiments. A substantially purified compound also includes those that are also free of other impurities in addition to salts such that the compound of interest is at least 98% pure in some embodiments, at least 99% pure in other embodiments, and at least 99.5% pure in still further embodiments.

As used herein, the term "liquid fraction" refers to a centrate or supernatant liquid obtained upon removal of solid mass from the fermentation broth. Solid mass removal includes, some, substantially all, or all of a solid mass. For example, in centrifugation, the liquid fraction is the centrate or supernatant which is separated from the solids. The liquid fraction is also the portion that is the permeate or supernatant obtained after filtration through a membrane. The liquid fraction is also the portion that is the filtrate or supernatant obtained after one or more filtration methods have been applied.

As used herein, the term "solid fraction" refers to a portion of the fermentation broth containing insoluble materials. Such insoluble materials include, for example, cells, cell debris, precipitated proteins, fines, and the like. Fines refer to small, usually amorphous solids. Fines can also be created during crystallization or during removal of water from the fermentation broth. Fines can be made up of a compound of interest which can be dissolved and recrystallized out. Fines can include portions of the solid fraction that are too small to be captured in a membrane filtration.

As used herein, the term "salts," used interchangeably with media salts and fermentation media salts, refers to the dissolved ionic compounds used in a fermentation broth. Salts in a fermentation broth can include, for example, sodium chloride, potassium chloride, calcium chloride, ammonium chloride, magnesium sulfate, ammonium sulfate, and buffers such as sodium and/or potassium and/or ammonium salts of phosphate, citrate, acetate, and borate.

As used herein, the term "substantially all" when used in reference to removal of water or salts refers to the removal of at least 95% of water or salts. "Substantially all" can also include at least 96%, 97%, 98%, 99%, or 99.9% removal or any value in between.

As used herein, the term "gene disruption" or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene with results in a truncated gene product or by any of various mutation strategies that inactivate the encoded gene product. One particularly useful method of gene disruption is complete gene deletion because it reduces or eliminates the occurrence of genetic reversions in the non-naturally occurring microorganisms of the invention.

As used herein, the term "microorganism" is intended to mean a prokaryotic or eukaryotic cell or organism having a microscopic size. The term is intended to include bacteria of all species and eukaryotic organisms such as yeast and fungi. The term also includes cell cultures of any species that can be cultured for the production of a biochemical.

As used herein, the term "1,4-BDO-producing microorganism" is intended to mean a microorganism engineered to biosynthesize 1,4-BDO in useful amounts. The engineered organism can include gene insertions, which includes plasmid inserts and/or chromosomal insertions. The engineered organism can also include gene disruptions to further optimize carbon flux through the desired pathways for production of 1,4-BDO. 1,4-BDO-producing organisms can include combination of insertions and deletions.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

In some embodiments, the invention provides a process of purifying a compound of interest from a fermentation broth. Applicable compounds include those having a boiling point higher than water and a low salt solubility. Compounds of interest also include those that are water miscible. An exemplary compound of interest is 1,4-BDO. The process includes separating a liquid fraction which contains the product of interest, from a solid fraction which includes the cells mass. The product of interest can be any compound having a higher boiling point than water. The cell mass includes the microbial organisms used in the production of the compound of interest. The solid fraction also includes cell debris, fines, proteins, and other insoluble materials from the fermentation.

The isolation process also includes removing the salts and water from the liquid fraction. The order in which they are removed is inconsequential. In some embodiments, there can be partial removal of salts, followed by removal of substantially all the water, and then the remaining salts. In other embodiments, there can be partial removal of water, followed by removal of substantially all of the salts, and then the remaining water. In other embodiments, water can be partially removed prior to separation of the solid fraction from the fermentation broth. In still other embodiments, final removal of substantially all the water can be done as part of the purification steps, for example by distillation. As disclosed below in Example VI, neat 1,4-BDO does not appreciably solubilize typical fermentation media salts. Thus, 1,4-BDO can be separated from salts by evaporation of the water from the liquid fraction. As shown in Example V below, salts begin to crystallize out when 1,4-BDO concentrations are about 30% by weight. In some embodiments, 1,4-BDO is a least 98% salt free upon separation of 1,4-BDO from salts crystallized or precipitated by water removal. As can be seen from Example VI, closely related homologues ethanediol and propane diol still appreciably solubilize fermentation salts. Thus, other methods can be employed to remove salts even after removal of substantially all the water.

Eventually when the salts and water have been removed, the remaining liquid or solid can undergo final purification. When the product of interest is a liquid, purification can be accomplished by distillation including by fractional distillation or multiple distillation, for example. When the product of interest is a solid, purification can be accomplished by recrystallization.

The overall process for producing and isolating a compound of interest and recycling various components of the fermentation broth are summarized in the block flow diagram of FIG. 1. Step 100 is fermentation utilizing carbon feedstock, such as sucrose, to produce the compound of interest. Step 110 is the separation of cells from the fermentation broth providing a liquid fraction, with Step 115 as an optional recycle of the cells. Step 110 has been exemplified in Examples I and II in which cells and solids are separated form fermentation broth by centrifugation and ultrafiltration. In Step 120, salts are separated from the liquid fraction, with Step 125 as an optional recycle of the salts. Step 120 has been exemplified in Examples III-V, which describe nanofiltration (Example III) and ion exchange (Example IV), in which water is still present in the liquid fraction. Example V shows the separation of salts through crystallization during water evaporation. Step 130 is the removal of water via evaporation, with Step 135 as an optional recycle of the water. Step 130 is exemplified by Example V, which show the evaporation of water which facilitates salt separation by precipitation. The order of Steps 120 and 130 are interchangeable as described further below. Finally in step 140 the compound of interest undergoes final purification.

In some embodiments, a process of isolating a compound of interest, including 1,4-BDO, from a fermentation broth involves separating a liquid fraction enriched in the compound of interest from a solid fraction that includes cells. In separating a liquid fraction enriched in the compound of interest, any amount of the fermentation broth can be processed including 1%, 5%, 10%, 20%, 30%, 40%, 50%, 60%, 70%, 80%, 90%, including up to the entirety of the volume of the fermentation broth and all values in between, and further including volumes less than 1% of the total volume of the fermentation broth. One skilled in the art will recognize that the amount of fermentation broth processed can depend on the type of fermentation process, such as batch, fed batch, or continuous, as detailed below. Separation of solids which includes cells and other solid byproducts and impurities from the fermentation broth can be accomplished by centrifugation, filtration, or a combination of these methods.

Figure 2:
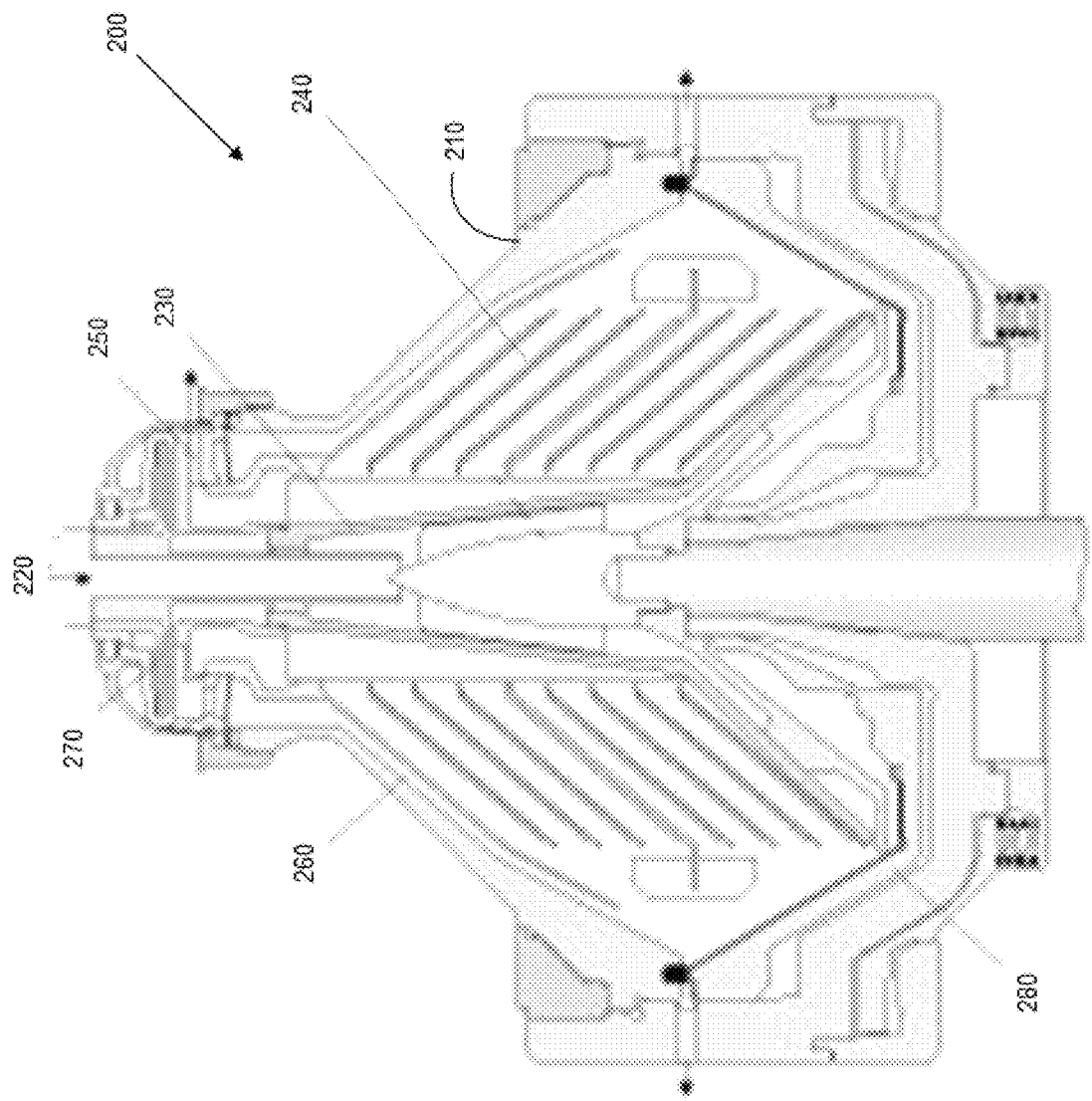
FIG. 2 shows a cross-section view of disc-stack centrifuge.

In some embodiments, centrifugation can be used to provide a liquid fraction comprising the compound of interest, such as 1,4-BDO, substantially free of solids including the cell mass. Depending on the centrifuge configuration and size, operating speeds can vary between 500 to 12,000 rpm which produce a centrifugal force of up to 15,000 times the force of gravity. Many centrifuge configurations for removal of cells and solids from a fermentation broth are known in the art. One such configuration, for example, is the disc-stack centrifuge 200 shown in FIG. 2.

Separation in a disc-stack centrifuge takes place inside a rotating bowl 210. The feed is introduced to the rotating bowl from the top via a stationary inlet pipe 220, and is accelerated in the distributor 230, before entering the disc stack 240. The distributor is designed accelerate the feed liquid.

The separation of liquid-solids or liquid-liquid-solids takes place between the discs. In a two phase system, such as with immiscible oil and water phase, the oil phase moving through the disc stack to the centre and can be discharged through pipes 250 and sprayed out into a collecting frame. The water and solids separated from the oil move to the periphery, the water is led via channels in the top disc 260 to the paring chamber, where it is pumped out of the rotor with means of a built-in paring disc 270.

The solids are collected in the periphery, from where it can be discharged intermittently via a centrifuge cyclone. The solids discharge can be achieved by a hydraulic system which at preset suitable intervals forces the sliding bowl bottom 280 to drop down opening the solids port at the bowl periphery.

A disc stack centrifuge separates solids and one or two liquid phases from each other, typically in a continuous process. The denser solids are forced outwards by centrifugal forces while the less dense liquid phases form inner concentric layers. By inserting special plates (disc stack) separation efficiency is increased. The solids can be removed manually, intermittently or continuously. In accordance with some embodiments, the cell mass can be introduced back into the fermentation. In a typical disc-stack centrifuge apparatus, the liquid phase overflows in an outlet area on top of a bowl into a separate chamber.

During operation of a disc-stack centrifuge, feed is introduced at the axis of the bowl, accelerated to speed, often by a radial vane assembly, and flows through a stack of closely spaced conical disks. Disk spacing is often between 0.5 to 3 mm in order to reduce the distance needed for separating settling particles from the fluid. The disc angle is often between 40 and 50 degrees to facilitate solids transport down the disk surface into the solids holding space.

The separating mechanism is based on the settling of solids under the influence of centrifugal force against the underside of the disks and slide down the disk into the solids hold space. Concurrently the clarified fluid moves up the channel between the disks and leaves the centrifuge via a centripetal pump. The settled solids are discharged either continuously though nozzles or intermittently through ports at the bowl periphery.

The disc-stack centrifuge can be used at low concentration and particle size of cells in a fermentation broth. A disc-stack centrifuge can be employed when the cell and other solid mass includes as little as about 0.2% to about 3% by weight of the fermentation broth. The disc-stack centrifuge can also be used when the cell and other solid mass is less than about 0.2% by weight, for example, 0.01%, 0.05%, and 0.1% by weight, including all values in between. The disc-stack centrifuge can also be used when the cell and other solid mass is more than 3% by weight, for example, 4%, 5%, 6%, 7%, 8%, 9%, 10%, and 15% by weight, including all values in between. When the combined cell mass and other solids is higher than about 3% to about 15% by weight other centrifugation configurations can be used, such as a decanter centrifuge.

Cells and other solid particles that are soft, plastic, and not abrasive, ranging from about 0.5 microns to about 500 microns are generally well-suited for disc-centrifugation. For particulate matter less than about 0.5 microns, ultrafiltration is useful. Likewise, above about 500 microns, a decanter-type centrifuge can be useful. The size of a typical prokaryotic cell that can be cultured to produce a compound of interest, including 1,4-BDO, can range in size from about 0.5 microns to about 10 microns, making disc-stack centrifugation a well-suited method.

Following batch, or during fed-batch or continuous fermentation, cells and insoluble solids can be removed from the fermentation broth by a disc-stack centrifuge. Outputs from a disc-stack centrifuge are a clarified (cell-free) centrate and an underflow stream containing about 5% to about 50% solids. The underflow solids stream from the disc stack centrifuge can contain a significant amount of the product of interest which can be recovered. One way to recover additional compound of interest from the solids is to include further centrifugation steps. In addition to providing greater recovery of the compound of interest, multiple centrifugation also serves to further concentrate the cells and solids. The concentrated cells can be recycled back to the fermentation. Cell recycle is particularly useful when valuable engineered organisms are being used.

In some embodiments, a decanter centrifuge can be employed to separate out the cells and solids. Good performance with a decanter centrifuge is normally realized with solids having particle sizes with a lower limit approaching about 10 microns, although smaller particles can be processed depending on their settling speed as described further below. This centrifuge configuration can be used when the cells of a culture are at the larger size range of a typical prokaryotic organism. One skilled in the art will appreciate that eukaryotic cells are often much larger than prokaryotic cells, with an average eukaryotic cell ranging in size from about 10 microns to about 100 microns or larger. Although a disc-stack centrifuge can operate well in this size range, a decanter centrifuge is useful because it is able to handle larger amounts of solids. Thus, when the cell mass plus other solids is more than about 3 to about 50% of the mass by weight, a decanter centrifuge can be used. This concentration applies to the underflow of the disc stack centrifuge described above, making a decanter centrifuge a well suited method to further concentrate the cell mass and recover additional product.

Figure 3:
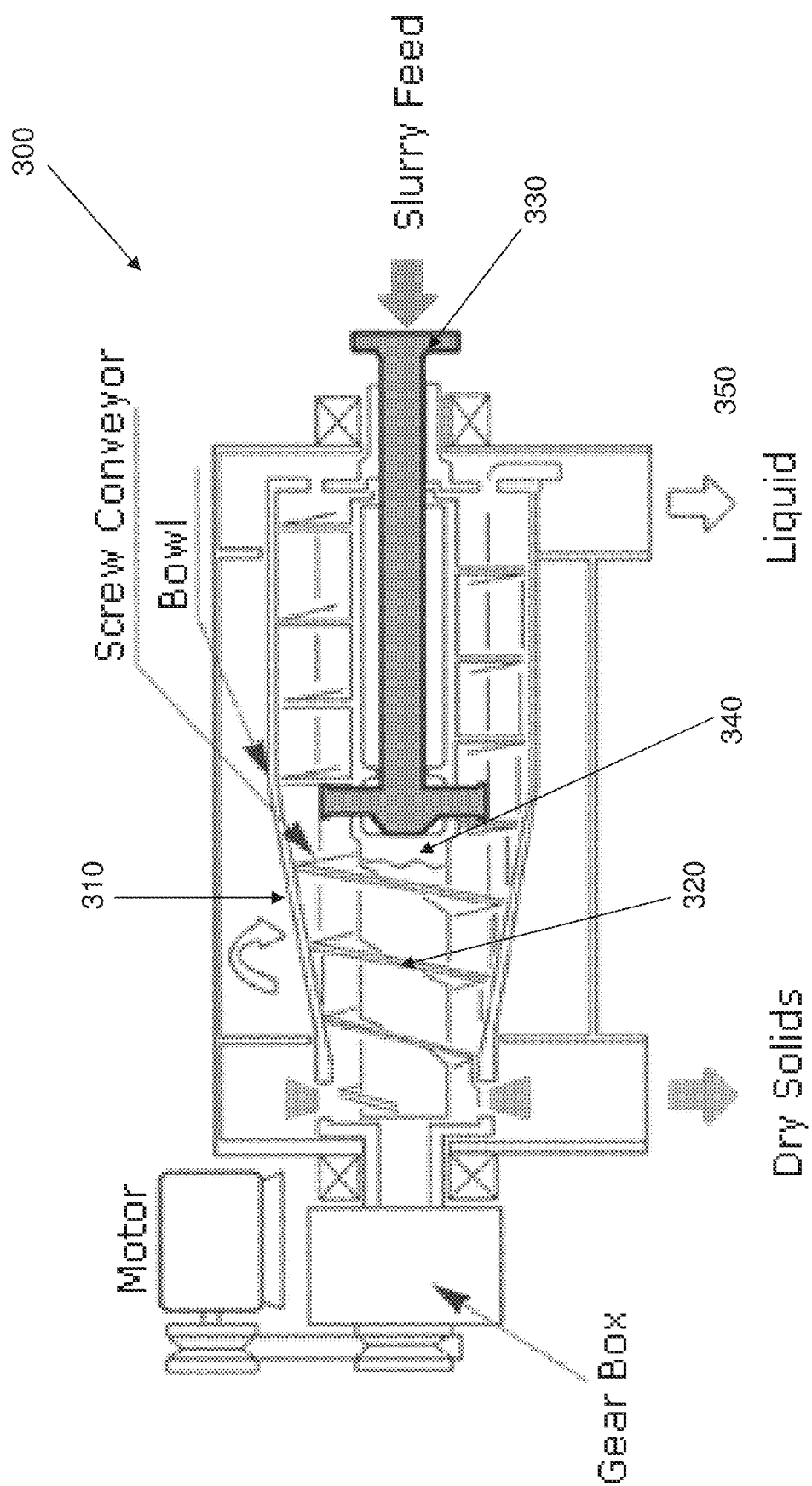
FIG. 3 shows a cross-section view of a decanter centrifuge.
Figure 4:
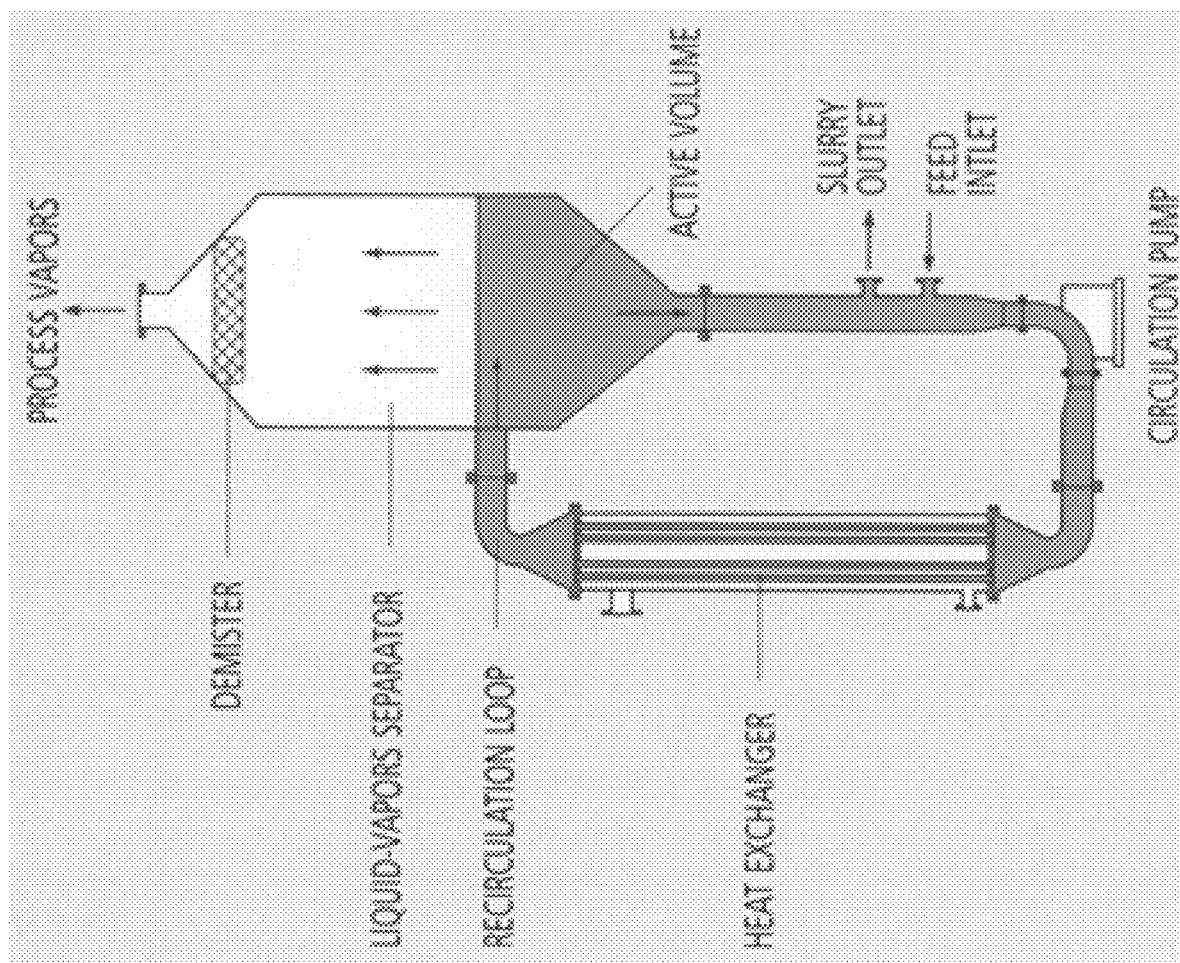
FIG. 4 shows a diagram of a forced circulation crystallizer.

The decanter, or solid bowl, centrifuge operates on the principle of sedimentation. Exemplary apparatus are described in U.S. Pat. Nos. 4,228,949 and 4,240,578, which are incorporated herein by reference in their entirety. In such an apparatus 300, as shown in FIG. 3, the central part of the machine is a rotating drum 310, which contains an independently rotating screw, 320. The fermentation broth or solids-containing feed, such as the underflow from the disc stack centrifuge, is fed via the inlet pipe 330 to the mixing chamber 340 in the core of the first part of the screw. The broth then passes through ports in the mixing chamber out towards the outer walls of the drum. The dewatered broth is transported out through the machine by the screw. The centrate 350, or supernatant, is decanted from the inner surface of the pond through centrate pipes. The water level in the drum can be adjusted in accordance with the characteristics of the material to be processed.

The drum and the screw rotate independently of one another at speeds up to about 3,600 rpm, depending on the type and size of machine. The dewatering principles used are known in the art as the "concurrent" or "counter-current" method. The concurrent method permits very low differential speeds. The differential speed is the difference between the speed of the drum and the speed of the screw. Low differential speeds mean longer residence times in the centrifuge, which result in drier sludge and considerably less wear. The counter-current principle can be more suitable for a feed that is easy to dewater and when a high capacity is desired.

Solids can be separated in solid bowl centrifuges provided their sedimentation speed in the liquid phase portion of the feed is sufficient. Factors that influence sedimentation speed include, for example, particle size, shape, differences in density between the cells/solids and the fermentation broth liquid phase, and viscosity. The geometry of the bowl, especially the relation between the length and diameter, are adaptable to suit the particular conditions. In some embodiments, good results can be obtained at length diameter ratio ranging from about 2:1 to about 3:1.

In operation, separation takes place in a horizontal conical cylindrical bowl equipped with a screw conveyor. The fermentation broth is fed into the bowl through a stationery inlet tube and accelerated by an inlet distributor. Centrifugal force provides the means for sedimentation of the solids on the wall of bowl. A conveyor, rotating in the same direction as bowl with differential speed, conveys the solids to the conical end. The solids are then lifted clear of the liquid phase and centrifugally dewatered before being discharged into a collecting channel. The remaining liquid phase then flows into a housing through an opening in cylindrical end of the bowl.

As described above, the cells and solids can be separated by multiple centrifugation to increase the isolated yield of the compound of interest. Multiple centrifugation can include centrifugation twice, three times, four times, and five times, for example. Intermediate underflow streams can be diluted with water to further increase recovery of the liquid product. Any combination of centrifugation configurations can also be used to perform multiple centrifugations, such as combinations of the disc-stack and decanter centrifugations described above. Further solids that are not separable by centrifugation can be removed through a filtration process, such as ultrafiltration.

Ultrafiltration is a selective separation process through a membrane using pressures up to about 145 psi (10 bar). Useful configurations include cross-flow filtration using spiral-wound, hollow fiber, or flat sheet (cartridge) ultrafiltration elements. These elements consist of polymeric or ceramic membranes with a molecular weight cut-off of less than about 200,000 Daltons, for example Hydranautics 5K PES membrane as used in Example I below. Ceramic ultrafiltration membranes are also useful since they have long operating lifetimes of up to or over 10 years. Ceramics have the disadvantage of being much more expensive than polymeric membranes. Ultrafiltration concentrates suspended solids and solutes of molecular weight greater than about 1,000 Daltons. Ultrafiltration includes filtering through a membrane having nominal molecular weight cut-offs (MWCO) from about 1,000 Daltons to about 200,000 Daltons (pore sizes of about 0.005 to 0.1 microns). The term molecular weight cut-off is used to define the size of protein that will be approximately 90% retained by the membrane. Using ultrafiltration the permeate liquid will contain low-molecular-weight organic solutes, such as 1,4-BDO, media salts, and water. The captured solids can include, for example, residual cell debris, DNA, and proteins.

In addition to the use ultrafiltration downstream of centrifugation, ultrafiltration can also be used downstream of microfiltration. Microfiltration provides an alternate means to centrifugation for separating cells. Microfiltration usually involves a low-pressure cross-flow membrane process for separating colloidal and suspended particles in the range of about 0.05-10 microns. Microfiltration includes filtering through a membrane having pore sizes from about 0.05 microns to about 5.0 microns. Polymeric, ceramic, or steel microfiltration membranes can be used to separate cells. Ceramic or steel microfiltration membranes have long operating lifetimes including up to or over 10 years. Microfiltration can be used in the clarification of fermentation broth. Unlike ultrafiltration, microfiltration will generally not capture residual cell debris, DNA, and proteins. However, it is useful to use a series of filtration steps with gradually decreasing pore size in order to avoid fouling of the filter membranes. This is useful for optimizing reuse of the filter membrane. In some embodiments, a single ultrafiltration step can be used to remove both cell mass (in place of centrifugation or microfiltration) and residual cell debris, DNA, proteins, etc. Ceramic ultrafiltration elements are useful for this application due to their ability to tolerate the frequent cleaning cycles used in this mode of operation.

In some embodiments, a further filtration method called nanofiltration can be used to separate out certain salts. This process step can allow the recovery of certain media salts without prior evaporation of water, for example. Nanofiltration can separate salts, remove color, and provide desalination. In nanofiltration, the permeate liquid generally contains monovalent ions and low-molecular-weight organic compounds as exemplified by 1,4-BDO. Nanofiltration includes filtering through a membrane having nominal molecular weight cut-offs (MWCO) from about 100 Daltons to about 2,000 Daltons (pore sizes of about 0.0005 to 0.005 microns). One method for nanofiltration is cross-flow filtration using a spiral-wound element. There are several nanofiltration membranes available, for example the thin film composite nanofiltration membrane GE DK used in Example III below. The mass transfer mechanism in nanofiltration is diffusion. The nanofiltration membrane allows the partial diffusion of certain ionic solutes (such as sodium and chloride), predominantly monovalent ions, as well as water. Larger ionic species, including divalent and multivalent ions, and more complex molecules are substantially retained.

Since monovalent ions are partially diffusing through the nanofiltration membrane along with the water, the osmotic pressure difference between the solutions on each side of the membrane is not as great and this typically results in somewhat lower operating pressure with nanofiltration compared with, for example, reverse osmosis.

Nanofiltration not only removes a portion of the inorganic salts but can also remove salts of organic acids. The removal of organic acid byproducts can be important in the isolation process because such acids can catalyze or serve as a reactant in undesirable side reactions with a product of interest. In the context of specific embodiments related to the isolation of 1,4-BDO, for example, the removal of organic acids is particularly useful because it can prevent reactions such as esterification of the hydroxyl groups during the elevated temperatures of any downstream evaporation or distillation steps. These ester byproducts typically have higher boiling points than BDO resulting in yield losses to the heavies stream in distillation.

Nanofiltration can also separate the glucose or sucrose substrate from the product of interest, preventing degradation reactions during evaporation and distillation. These degradation reactions can produce coloration of the compound of interest. The salt and substrate rich nanofiltration retentate can be better suited for recycle to fermentation compared to a recovered salt stream from evaporative crystallization. For example, the use of filtration methods in lieu of methods involving application of heat can result in fewer degradation products. Such degradation products can be toxic to the fermentation organism.

Both nanofiltration and ion exchange can remove color forming compounds and UV absorbing compounds. This can be useful in the context of some compounds of interest. For example, color removal is useful in the production of polymer grade 1,4-BDO.

Multiple filtration membranes can be used serially with gradually increasing refinement of the size of the solids that are retained. This can be useful to reduce fouling of membranes and aid in recovering individual components of the fermentation broth for recycle. For example, a series of filtrations can utilize microfiltration, followed by ultrafiltration, followed by nanofiltration. Thus, microfiltration aids in recovery of cell mass, ultrafiltration removes large components such as cell debris, DNA, and proteins, and nanofiltration aids in recovery of salts.

Those skilled in the art will recognize that any of the various filtration types can be integrated within the context of a variety of fermentation bioreactor configurations given the teachings and guidance provide herein. In some embodiments the filtration occurs external to the bioreactor. In this mode, any amount of the fermentation broth can be removed from the bioreactor and filtered separately. Filtration can be aided by use of vacuum methods, or the use of positive pressure. In some embodiments, cell filtration can be accomplished by means of a filtration element internal to the bioreactor. Such configurations include those found in membrane cell-recycle bioreactors (MCRBs). Chang et al. U.S. Pat. No. 6,596,521 have described a two-stage cell-recycle continuous reactor.

In some embodiments, the cells can be separated and recycled into the fermentation mixture by means of an acoustic cell settler as described by Yang et al. (*Biotechnol. Bioprocess. Eng.*, 7:357-361(2002)). Acoustic cell settling utilizes ultrasound to concentrate the suspension of cells in a fermentation broth. This method allows for facile return of the cells to the bioreactor and avoids the issue of membrane fouling that sometimes complicates filtration-type cell recycle systems.

With respect to isolation of salts prior to water evaporation, other methods can be used alone, or in combination with the above exemplary filtration processes. Such other methods include, for example, ion exchange. For example, Gong et al. (*Desalination* 191:1-3, 193-199 (2006)) have described the effects of transport properties of ion-exchange membranes on desalination of 1,3-propanediol fermentation broth by electrodialysis.

Ion exchange elements can take the form of resin beads as well as membranes. Frequently, the resins are cast in the form of porous beads. The resins can be cross-linked polymers having active groups in the form of electrically charged sites. At these sites, ions of opposite charge are attracted but may be replaced by other ions depending on their relative concentrations and affinities for the sites. Ion exchangers can be cationic or anionic, for example. Factors that determine the efficiency of a given ion exchange resin include the favorability for a given ion, and the number of active sites available. To maximize the active sites, large surface areas are generally useful. Thus, small particles are useful because of their large surface area.

The resin polymer can include cross-linking on the order of about 0.5 to about 15 percent, for example. Temperature and pH also affect the efficiency of ion exchange. For example, pH can affect the number of ions available for exchange, and temperature affects the kinetics of the process. In some embodiments, salt removal by ion exchange includes removal of organic acids and salts of organic acids. The anionic form of organic acids can bind to an anion exchange active site. In some embodiments, the pH for binding an organic acid is below the pKa for that acid. The pKa of lactic acid, for example, is about 3.1. An effective method for removing salts of organic acids is cation exchange followed by anion exchange. The cation resin first removes the organic acid counter-ion (calcium, sodium, ammonium, and the like), lowering the pH of the solution. The anion resin then binds the free acid.

A useful aspect of ion exchange is the facility with which the resin can be regenerated. The resin can be flushed free of the exchanged ions and contacted with a solution of desirable ions to replace them. With regeneration, the same resin beads can be used over and over again, and the isolated ions can be concentrated in a waste effluent. As with the many filtration methods, serial ion exchange can be performed, as exemplified in Example IV. Thus, a feed can be passed through both any number of anionic and cationic exchangers, or mixed-bed exchangers, and in any order.

In some embodiments, water removal via evaporation is used to facilitate salt recovery. In some embodiments, the salts have been removed prior to water removal. In either case, evaporated water can be recycled as makeup water to the fermentation, minimizing the overall water requirements for the process. In the case where the salts have not been removed, their solubility in the 1,4-BDO enriched liquid phase is sufficiently low that they can crystallize after water removal. In some embodiments the salts have a sufficiently low solubility in 1,4-BDO that the separated 1,4-BDO is about 98% salt-free.

An evaporative crystallizer can be used to generate precipitated salts which can be removed by centrifugation, filtration or other mechanical means. In the context of 1,4-BDO isolation, an evaporative crystallizer serves to remove water from the fermentation broth creating a liquid phase that has removed enough water to cause supersaturation of the fermentation media salts and subsequent crystallization in the remaining liquid phase or mother liquor. As demonstrated in Example V below, crystallization of salts begins at a 1,4-BDO concentration of about 30% by weight.

The mother liquor refers to the bulk solvent in a crystallization. Frequently, the mother liquor is a combination of solvents with different capacity to solublize or dissolve various solutes. In the context of the purification of 1,4-BDO from a fermentation broth, for example, the mother liquor includes the liquid fraction obtained after removing cells and other solids from the fermentation broth. In the context of isolating a compound of interest from a fermentation broth, the primary solute includes the fermentation media salts and organic acids.

Supersaturation in crystallization refers to a condition in which a solute is more concentrated in a bulk solvent than is normally possible under given conditions of temperature and pressure. The bulk solvent of the fermentation broth is water containing relatively smaller amounts of 1,4-BDO, for example, and dissolved salts and other media.

Figure 5:
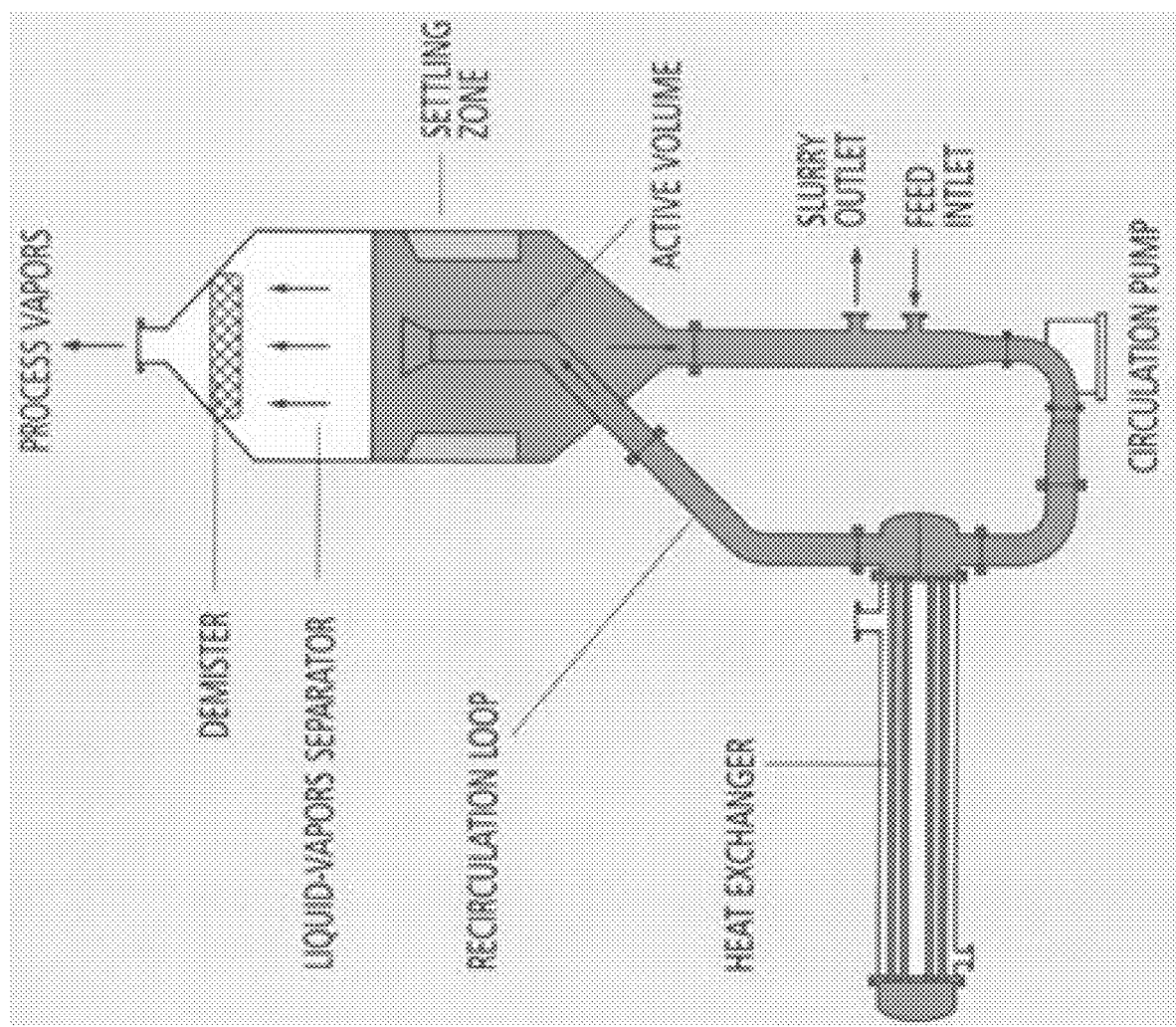
FIG. 5 shows a diagram of a forced circulation crystallizer with a horizontal heat exchanger and baffles in the active volume.
Figure 6:
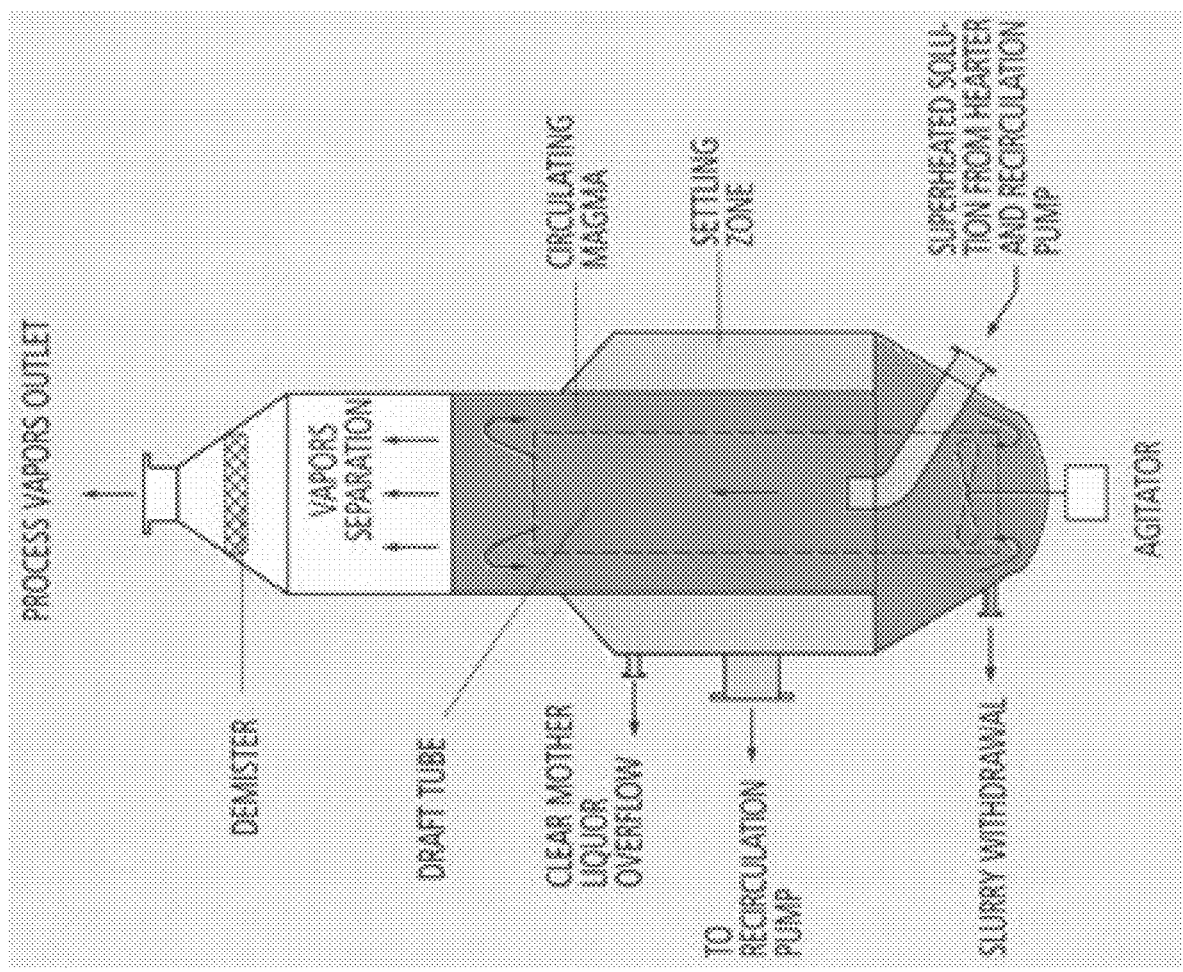
FIG. 6 shows a diagram of a draft tube and baffle crystallizer.

An exemplary evaporative crystallizer is the forced circulation (FC) crystallizer as shown in FIGS. 5 and 6. An FC crystallizer has been described, for example, in U.S. Pat. No. 3,976,430 which is incorporated by reference herein in its entirety. The FC crystallizer evaporates water resulting in an increased supersaturation of the salts in the compound-enriched (such as 1,4-BDO) liquid fraction thus causing the salts to crystallize. The FC crystallizer is useful for achieving high evaporation rates. The FC crystallizer consists of four basic components: a crystallizer vessel with a conical bottom portion, a circulating pump, a heat exchanger, and vacuum equipment which handles the vapors generated in the crystallizer. Slurry from the crystallizer vessel is circulated through the heat exchanger, and returned to the crystallizer vessel again, where supersaturation is relieved by deposition of salts on the crystals present in the slurry. The evaporated water is conducted to the vacuum system, where it is condensed and recycled to the fermentation broth as desired. Although in some embodiments, there is a low vacuum, it is also possible to use the FC crystallizer at about atmospheric pressure as well. In some embodiments, the FC crystallizer utilizes adiabatic evaporative cooling to generate salt supersaturation. In such embodiments, the FC crystallizer need not be equipped with a heat exchanger.

In some embodiments, the FC crystallizer can be further equipped with internal baffles, as shown in FIG. 6, to handle overflow of the liquid phase and to reduce fines which can inhibit crystal growth. The salts generated in the FC crystallizer can also be size selected with the aid of an optional elutriation leg. This portion of the FC crystallizer appears at the bottom of the conical section of the crystallizer vessel. Size selection is achieved by providing a flow of fermentation fluid up the leg allowing only particles with a particular settling rate to move against this flow. The settling speed is related to the size and shape of the crystals as well as fluid viscosity. In further embodiments, the FC crystallizer can also be equipped with an internal scrubber to reduce product losses. This can assist in the recovery of volatile products.

Figure 7:
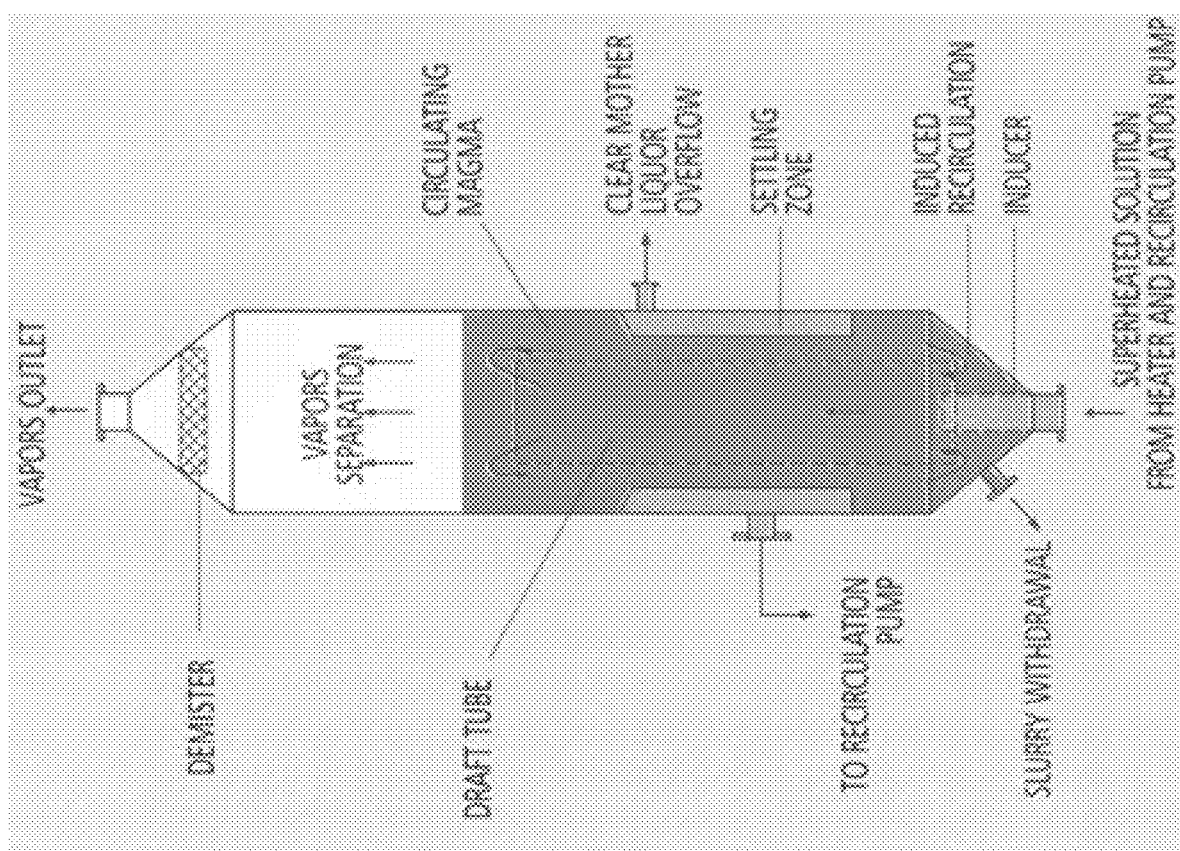
FIG. 7 shows a diagram of an induced circulation crystallizer.

The turbulence or draft tube and baffle "DTB" crystallizer, shown in FIG. 7, provides two discharge streams, one of a slurry that contains crystals, and another that is the liquid phase with a small amount of fines. The configuration of the DTB crystallizer is such that it promotes crystal growth, and can generate crystals of a larger average size than those obtained with the FC crystallizer. In some embodiments, the DTB crystallizer operates under vacuum, or at slight superatmospheric pressure. In some embodiments, the DTB crystallizer uses vacuum for cooling.

In some embodiments, a DTB crystallizer operates at a low supersaturation. One skilled in the art will appreciate that large crystals can be obtained under this regime. The system can be optionally configured to dissolve fines to further increase crystal size. When the DTB crystallizer is used in fermentation media salt recovery, crystal size is not necessarily a priority.

The DTB crystallizer has been studied widely in crystallization, and can be modeled with accuracy. Its distinct zones of growth and clarified liquid phase facilitate defining kinetic parameters, and thus, the growth and nucleation rate can be readily calculated. These features make the DTB crystallizer suitable to mathematical description, and thus, subject to good operating control. The DTB crystallizer is an example of a mixed suspension mixed product removal (MSMPR) design, like the FC crystallizer.

The DTB crystallizer includes a baffled area, serving as a settling zone, which is peripheral to the active volume. This zone is used to further process the liquid phase and fines. In some embodiments, the baffled area is not present, as can be the case where further processing of fines is less important. Such a configuration is known in the art as a draft-tube crystallizer. A DTB crystallizer can be equipped with an agitator, usually at the bottom of the apparatus in the vicinity of the entry of the feed solution. Like the FC crystallizer, the DTB crystallizer is optionally equipped with an elutriation leg. In some embodiments, an optional external heating loop can be used to increase evaporation rates.

Figure 8:
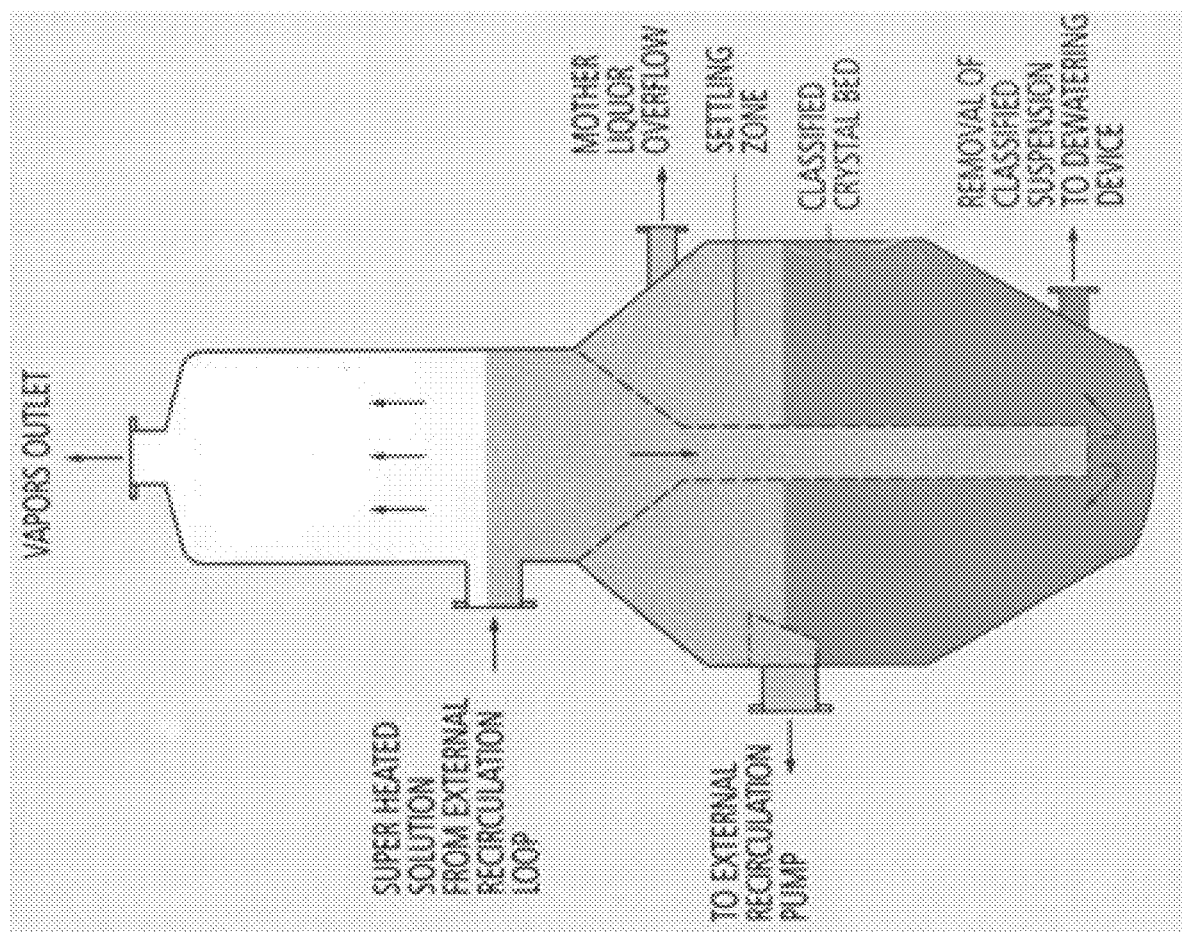
FIG. 8 shows a diagram of a close-type Oslo crystallizer.

Yet another crystallizer configuration is the induced circulation crystallizer as shown in FIG. 8. This configuration provides additional agitation means for the active volume. The apparatus is similar to the DTB crystallizer with respect to the use of a draft tube. Unlike the DTB apparatus, there is no internal agitator. Instead, an inducer in the conical portion of the vessel introduces heated solution from a recirculation pump. As with other crystallization apparatus configurations, the induced circulation crystallizer is optionally equipped with an elutriation leg. Baffles can also be optionally employed with this type of crystallizer.

Figure 9:
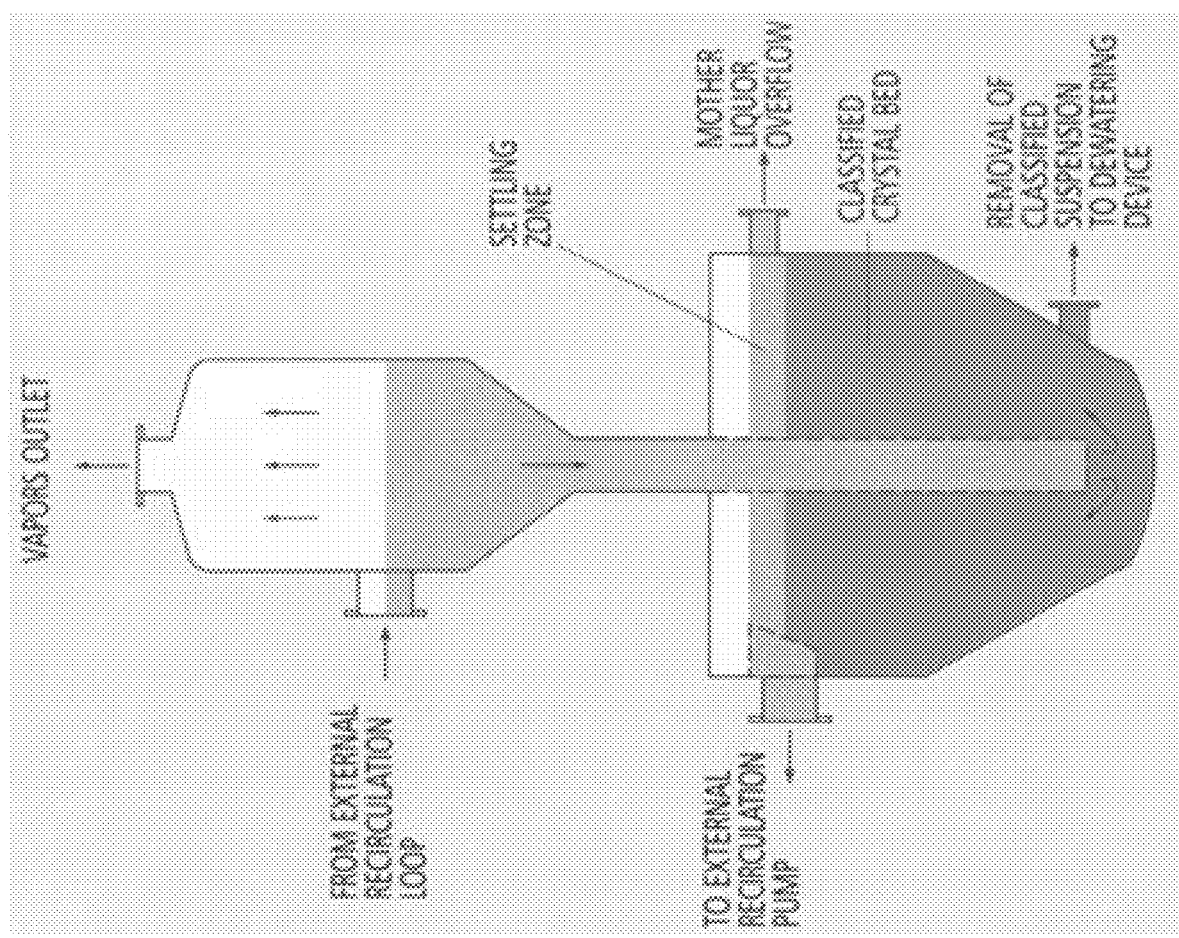
FIG. 9 shows a diagram of an open-type Oslo crystallizer.
Figure 10:
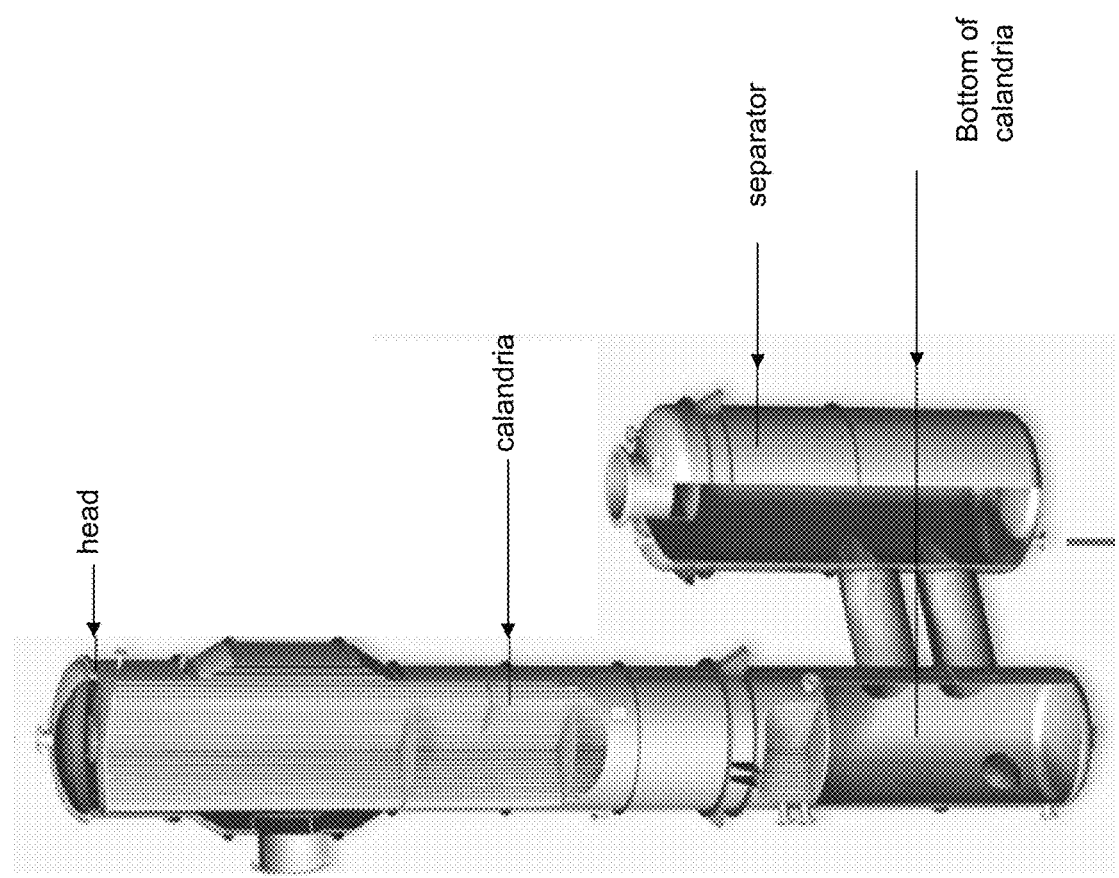
FIG. 10 shows a partial cross-section view of a falling film evaporator.

In still further embodiments, the crystallizer can be an Oslo-type crystallizer, as shown in FIGS. 9 and 10. This type of crystallizer is also referred to as "growth-", "fluid-bed-", or "Krystal-" type crystallizer. The Oslo crystallizer allows the growth of crystals in a fluidized bed, which is not subject to mechanical circulation. A crystal in an Oslo unit will grow to a size proportional to its residence time in the fluid bed. The result is that an Oslo crystallizer can grow crystals larger than most other crystallizer types. The slurry can be removed from the crystallizer's fluidized bed and sent to, for example, a centrifugation section. Clear liquid phase containing 1,4-BDO can be purged from the crystallizer's clarification zone.

The classifying crystallization chamber is the lower part of the unit. The upper part is the liquor-vapor separation area where supersaturation is developed by the removal of water. The slightly supersaturated liquid phase flows down through a central pipe and the supersaturation is relieved by contact with the fluidized bed of crystals. The desupersaturation occurs progressively as the circulating liquid phase moves upwards through the classifying bed before being collected in the top part of the chamber. The remaining liquid leaves via a circulating pipe and after addition of the fresh feed, it passes through the heat exchanger where heat make-up is provided. It is then recycled to the upper part.

In some embodiments, the Oslo type crystallizer can also be optionally equipped with baffles, an elutriation leg, and scrubber as described above. Since the growing crystals are not in contact with any agitation device, the amount of fines to be destroyed is generally lower. The Oslo type crystallizer allows long cycles of production between periods for crystal removal.

The Oslo-type crystallizer is useful for the separation-crystallization of several chemical species as would be found in fermentation media salts. In one embodiment, the Oslo type crystallization unit is of the "closed" type, as shown in FIG. 9. In other embodiments the Oslo-type crystallizer is the "open" type as shown in FIG. 10. The latter configuration is useful when large settling areas are needed, for example.

Many of the foregoing evaporative crystallization apparatus allow for controlled crystal growth. In the recovery of fermentation media salts from the liquid portion after cell removal, the exact crystal morphology, size, and the like are generally inconsequential. Indeed, recovery of amorphous media salts can be sufficient in the purification of any compound of interest, including 1,4-BDO. Thus, in some embodiments, other evaporation methods can be utilized that do not control crystal growth per se.

When salts are removed by nanofiltration and/or ion exchange, a reverse osmosis (RO) membrane filtration can be used to remove a portion of the water prior to evaporation. Water permeates the RO membrane while 1,4-BDO is retained. In some embodiments, an RO membrane can concentrate a product, such as 1,4-BDO to about 20%. One skilled in the art will recognize that the osmotic pressure from the product 1,4-BDO increases to a point where further concentration using an RO membrane is no longer viable. Nonetheless, the use of an RO membrane is a useful low energy input method for concentrating the product of interest prior to the more energy intensive water evaporation process. Thus, on large scale, employing a RO membrane is particularly useful.

In some embodiments, substantially all of the salts are removed prior to removal of water. In other embodiments, substantially all of the salts are removed after removal of a portion of water. The portion of water removed can be any amount including 5%, 10%, 15%, 20%, 25%, 30%, 35%, 40%, 50%, 60%, 70%, 80%, and all values in between. In some embodiments, salts are removed after removal of substantially all of the water. Substantially all the water includes 95%, 96%, 97%, 98%, 99%, 99.9% and all values in between and including all the water.

There are many types and configurations of evaporators available for water removal. One consideration for designing an evaporation system is minimizing energy requirements. Evaporation configurations such as multiple effects or mechanical vapor recompression allow for reduced energy consumption. In some embodiments, removing water is accomplished by evaporation with an evaporator system which includes one or more effects. In some embodiments, a double- or triple-effect evaporator system can be used to separate water from a product of interest, such as 1,4-BDO.

Any number of multiple-effect evaporator systems can be used in the removal of water. These apparatus can also be applied to any fermentation product that having a boiling point higher than water. A triple effect evaporator, or other evaporative apparatus configuration, can include dedicated effects that are evaporative crystallizers for salt recovery, for example the final effect of a triple effect configuration.

An evaporator is a heat exchanger in which a liquid is boiled to give a vapor that is also a low pressure steam generator. This steam can be used for further heating in another evaporator called another "effect." Thus, for example, two evaporators can be connected so that the vapor line from one is connected to the steam chest of the other providing a two, or double-effect evaporator. This configuration can be propagated to a third evaporator to create a triple-effect evaporator, for example.

Evaporators can therefore be classified by the number of effects. In a single-effect evaporator, steam provides energy for vaporization and the vapor product is condensed and removed from the system. In a double-effect evaporator, the vapor product off the first effect is used to provide energy for a second vaporization unit. The cascading of effects can continue for any number of stages. Multiple-effect evaporators can remove large amounts of solvent more efficiently relative to a single effect evaporator.

In a multiple effect arrangement, the latent heat of the vapor product off of an effect is used to heat the following effect. Effects are numbered beginning with the one heated by steam, Effect I. The first effect operates under the highest pressure. Vapor from Effect I is used to heat Effect II, which consequently operates at lower pressure. This continues through each addition effect, so that pressure drops through the sequence and the hot vapor will travel from one effect to the next.

In some embodiments, all effects in an evaporator can be physically similar in size, construction, and heat transfer area. Unless thermal losses are significant, they can also have the same capacity as well. Evaporator trains, the serially connected effects, can receive feed in several different ways. Forward Feed arrangements follow the pattern I, II, and III. These use a single feed pump. In this configuration the feed is raised to the highest operating temperature as used in Effect I. The lowest operating temperature is in the final effect, where the product is also most concentrated. Therefore, this configuration is useful for products that are heat sensitive or to reduce side reactions.

In other embodiments, Backward Feed arrangements, III, II, I can be used. In such a configuration multiple pumps are used to work against the pressure drop of the system, however, since the feed is gradually heated they can be more efficient than a forward feed configuration. This arrangement also reduces the viscosity differences through the system and is thus useful for viscous fermentation broths. In some embodiments, Mixed Feed arrangements can be utilized, with the feed entering in the middle of the system, or effects II, III, and I. The final evaporation is performed at the highest temperature. Additionally, fewer pumps are required than in a backward feed arrangement. In still further embodiments, a Parallel Feed system is used to split the feed stream and feed a portion to each effect. This configuration is common in crystallizing evaporators where the product is expected to be a slurry.

Figure 11:
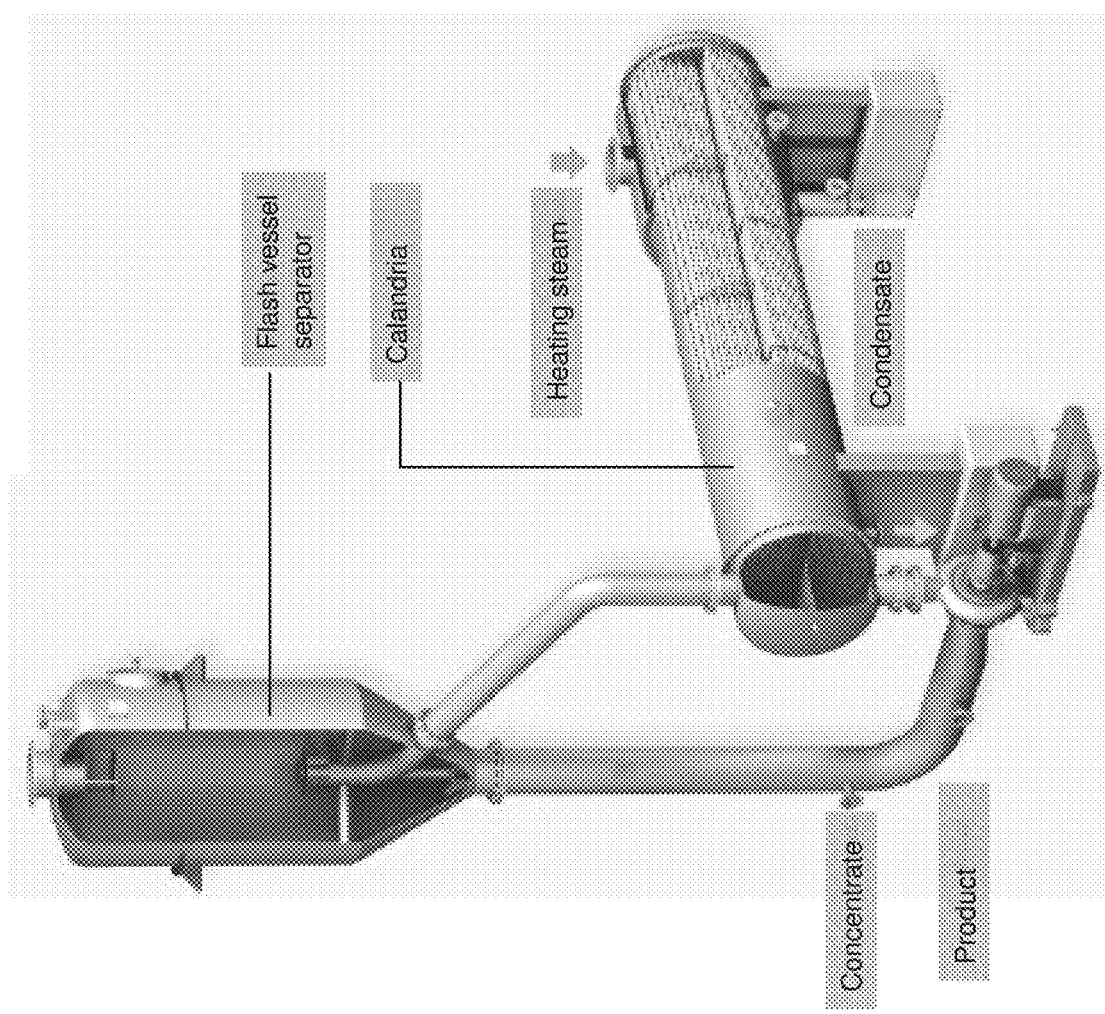
FIG. 11 shows a partial cross-section view of a forced circulation evaporator.

There are numerous evaporator designs. Any combination of designs can be used as an effect as described above. One evaporator design is the falling film evaporator. This apparatus includes a vertical shell-and-tube heat exchanger, with a laterally or concentrically arranged centrifugal separator as shown in FIG. 11.

The liquid to be evaporated is evenly distributed on the inner surface of a tube. The liquid flows downwards forming a thin film, from which evaporation takes place because of the heat applied by the steam. The steam condenses and flows downwards on the outer surface of the tube. A number of tubes are built together side by side. At each end the tubes are fixed to tube plates, and finally the tube bundle is enclosed by a jacket.

The steam is introduced through the jacket. The space between the tubes forms the heating section. The inner side of the tubes is called the boiling section. Together they form the calandria. The concentrated liquid and the vapor leave the calandria at the bottom part, from where the main proportion of the concentrated liquid is discharged. The remaining part enters the subsequent separator tangentially together with the vapor. The separated concentrate is discharged, usually be means of the same pump as for the major part of the concentrate from the calandria, and the vapor leaves the separator from the top. The heating steam, which condenses on the outer surface of the tubes, is collected as condensate at the bottom part of the heating section, from where it is discharged.

Falling film evaporators can be operated with very low temperature differences between the heating media and the boiling liquid, and they also have very short product contact times, typically just a few seconds per pass. These characteristics make the falling film evaporator particularly suitable for heat-sensitive products. Operation of falling film evaporators with small temperature differences facilitates their use in multiple effect configurations or in conjunction with mechanical vapor compression systems.

Sufficient wetting of the heating surface in tubes of the calandria helps avoid dry patches and incrustations which can clog the tubes. In some embodiments, the wetting rate can be increased by extending or dividing the evaporator effects. Falling film evaporators are highly responsive to alterations of parameters such as energy supply, vacuum, feed rate, and concentrations, for example. In some embodiments, a single, double, triple, or other multiple-effect falling film evaporator configuration can utilize fermentation feed that has been filtered through a nanofiltration process as detailed above. Reducing the salts prior to water evaporation can further help prevent incrustation in the tubes of the calandria.

In some embodiments, the falling film evaporator is a short path evaporator. In operation the liquid fraction is evenly distributed over the heating tubes of the calandria by means of a distribution system. The liquid fraction flows down in a thin film on the inside walls in a manner similar to the conventional falling film evaporator. The vapors formed in the in the calandria tubes are condensed as a distillate on external walls of condensate tubes and then flows downward. Water distillate and the enriched liquid fraction are separately discharged from the lower part of the evaporator.

Figure 12:
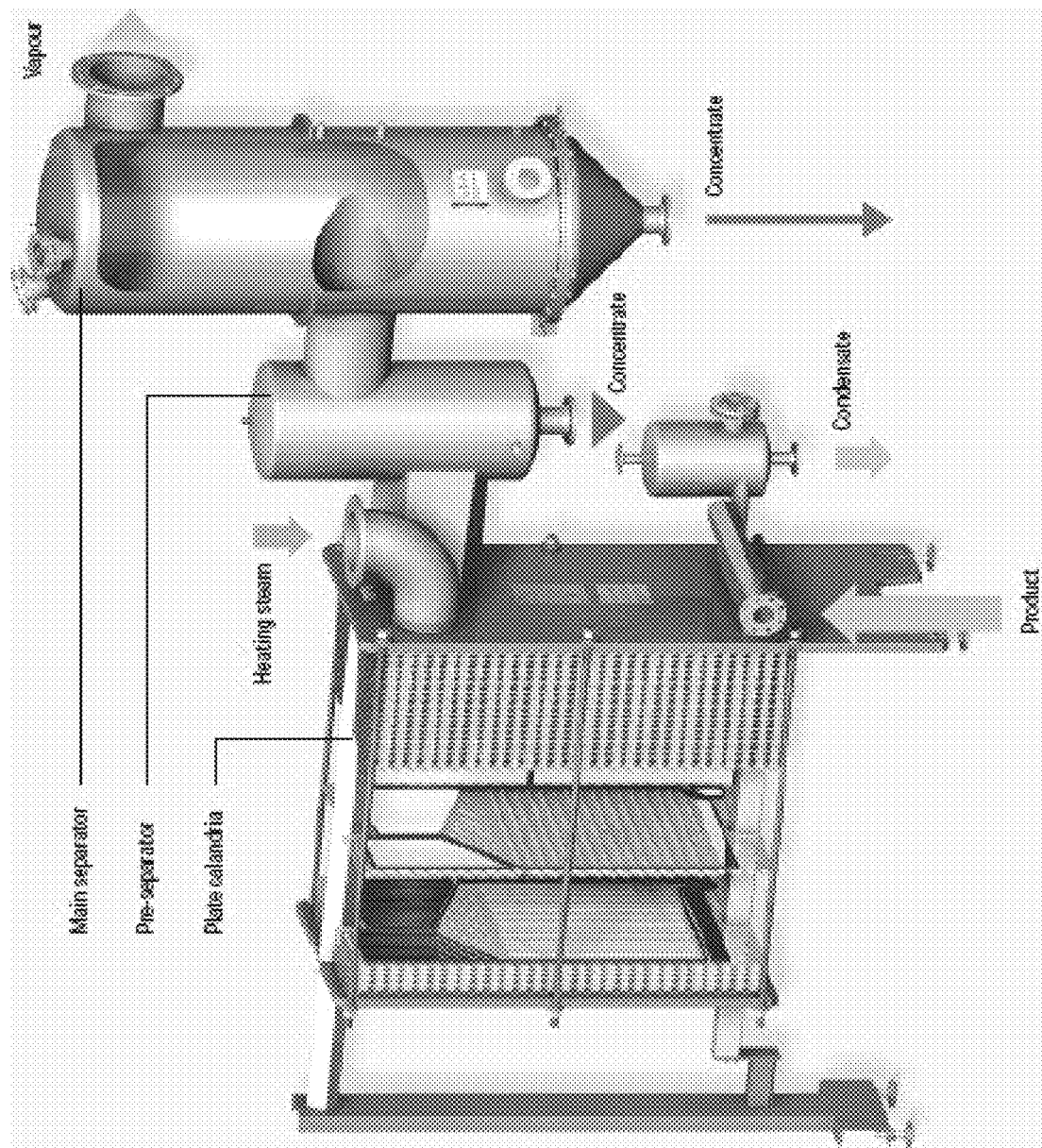
FIG. 12 shows a partial cross-section view of a plate evaporator.

Another evaporator configuration is the forced circulation evaporator. In this design a flash vessel or separator is disposed above a calandria and circulation pump as shown in FIG. 12. In operation, the liquid fraction is circulated through the calandria by means of a circulation pump. The liquid is superheated within the calandria at an elevated pressure higher than the normal boiling pressure. Upon entering the separator, the pressure is rapidly reduced resulting in flashing or rapid boiling of the liquid. The flow velocity, controlled by the circulation pump, and temperatures can be used to control the water removal process. This configuration is useful for avoiding fouling of the calandria tubes.

In some embodiments, multiple forced circulation evaporator effects can be used as described above. For example, in addition to a single effect forced circulation evaporator, double, triple, and multiple effect forced circulation evaporators can be used in the separation of water from the liquid fraction of the fermentation liquid. In some embodiments, one or more forced circulation evaporators can be used in conjunction with one or more falling film evaporators.

Figure 13:
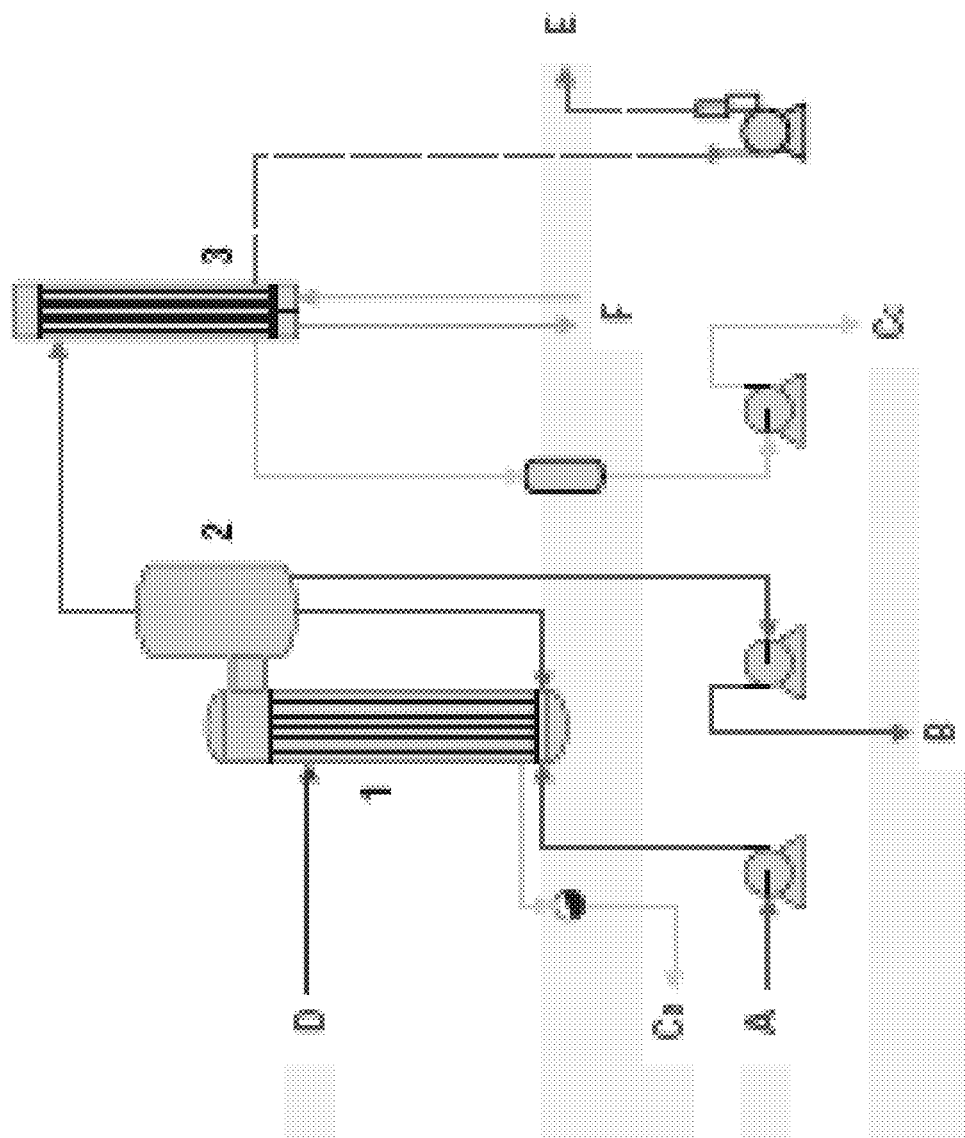
FIG. 13 shows a diagram of a circulation evaporator.

In still further embodiments, the evaporator can be a plate evaporator, as shown in FIG. 13. This evaporator uses a plate heat exchanger and one or more separators. A plate-and-frame configuration uses plates with alternating channels to carry heating media and the liquid fraction of the fermentation broth. In operation, the liquid phase and heating media are passed through their respective channels in counterflow. Defined plate distances and shapes generate turbulence resulting in efficient heat transfer. The heat transfer to the channels with the liquid fraction causes water to boil. The vapor thus formed drives the residual liquid as a rising film into a vapor duct of the plate assembly. Residual liquid and vapors are separated in the downstream centrifugal separator. The wide inlet duct and the upward movement assist in good distribution over the cross-section of the heat exchanger. A plate evaporator can be usefully operated with a pre-filtration through a nanofiltration membrane to avoid fouling. Thus, similar considerations as the falling film evaporator with respect to incrustation are warranted.

In some embodiments, multiple-effect plate evaporation can be utilized in much the same manner as described above for falling film and forced circulation evaporators. When used in multiple effect configurations, one skilled in the art will recognize the benefit of using a forced circulation evaporator and/or a nanofiltration step prior to introduction of the liquid fraction to a plate evaporator. Thus, a separation scheme can include, for example, nanofiltration, followed by a multiple-effect evaporation configuration of one or more forced circulation evaporators, followed by one or more of a plate and/or falling film evaporator. In still further embodiments, any of the evaporative crystallizers described above can also be used in conjunction with a multiple-effect configuration.

Figure 14:
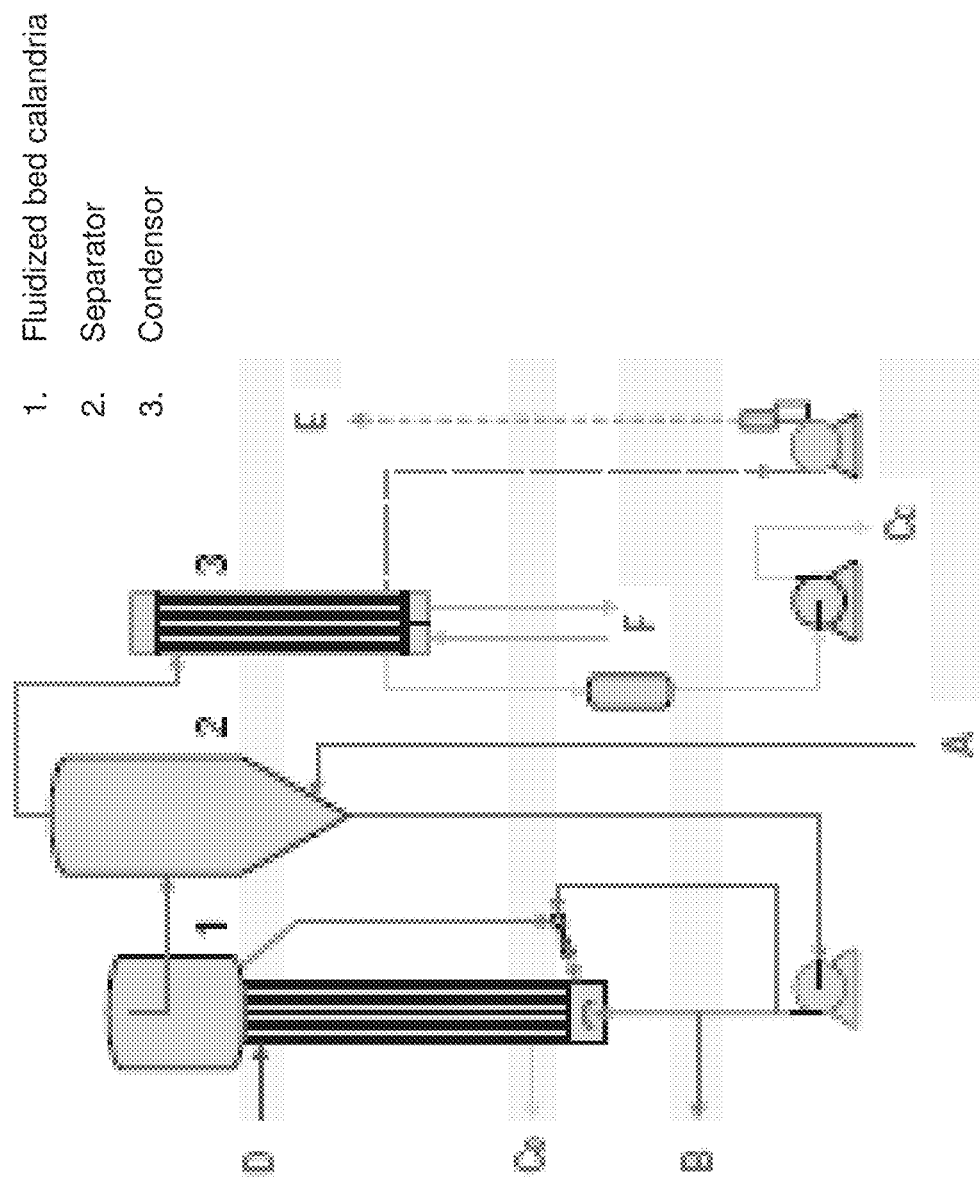
FIG. 14 shows a diagram of a fluidized bed evaporator.

In some embodiments, a circulation evaporator can be used to remove water from the liquid fraction as shown in FIG. 14. The circulation evaporator utilizes a vertical calandria with short tube length with a lateral separator disposed at the top of the heat exchanger. In operation the liquid fraction is supplied at the bottom of the calandria and rises to the top. During heating in the tubes of the calandria, the water begins to boil releasing vapor. The liquid is carried to the top of the calandria entrained by the upward moving vapors. The liquid is separated from the vapors as it enters the separator. The liquid flows back into the evaporator via a circulation pipe to allow continued circulation. The larger the temperature difference between the heating elements of the calandria and the separator chamber results in larger degree of water evaporation from the liquid fraction. When the liquid portion is sufficiently enriched in 1,4-BDO, the salts will begin to precipitate from the liquid fraction.

In some embodiments, the separator of the circulation evaporator can be partitioned into several separation chambers each equipped with its own liquid circulation system. This can reduce the heating surface needed to remove water from the liquid fraction.

Figure 15:
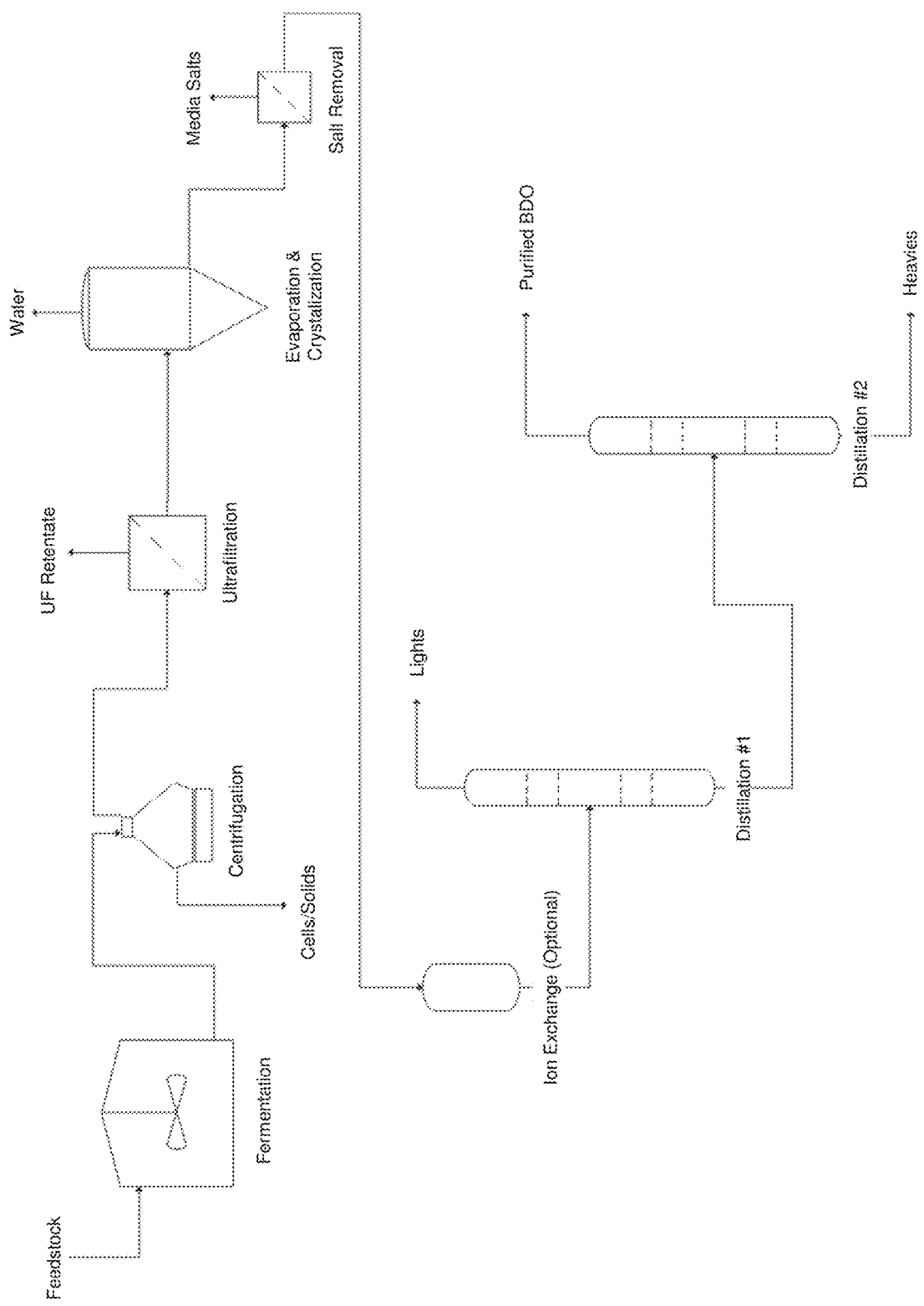
FIG. 15 shows a flow diagram of a complete scheme for the production and isolation of 1,4-BDO.

The fluidized bed evaporator is yet another configuration that can be used for water removal from the liquid fraction. Such a system, shown in FIG. 15, is equipped with a vertical fluidized bed heat exchanger. On the tube side of the heat exchanger are solid particles such as glass or ceramic beads, or steel wire particles.

The fluidized bed evaporator operates in a similar manner to the forced circulation evaporator. The upward movement of the liquid entrains the solid particles which provides a scouring or cleaning action. Together with the liquid fraction they are transferred through the calandria tubes. At the head of the calandria, the solid particles are separated from the liquid and are recycled to the calandria inlet chamber. The superheated fluid is flashed to boiling temperature in the separator allowing removal of water through evaporation. The scouring action of the solids in the tubes of the calandria allow for prolonged operation times and further retard fouling of the tubes. This can be useful when the creation of fouling solids limits the use of conventional forced circulation evaporator systems.

The rising film evaporator is yet another type of evaporator useful in the removal of water from the liquid fraction collected from the fermentation broth. This system configuration has a top-mounted vapor separator on a vertical shell-and-tube heat exchanger (calandria). In operation, the liquid fraction at the bottom of the calandria rises to the top to the vapor separator. External heating causes the water in the liquid fraction to boil in the inside walls of the calandria tubes. The upward movement of the steam causes the liquid fraction to be carried to the top of the calandria. During ascent though the tube further vapor is formed. Upon entry into the separator vapors and liquid phases are separated. The rising film evaporator is particularly useful when used with viscous liquids and/or when large amounts of fouling solids are expected.

The counterflow-trickle evaporator is yet another evaporator that can be used for water removal from the liquid fraction of the fermentation broth. This apparatus has a shell-and-tube heat exchanger (calandria) with the lower part of the calandria larger than that of a rising film evaporator. Disposed on top of the calandria, like the rising film evaporator is a separator. In this evaporator the separator is further equipped with a liquid distribution system.

In operation, liquid is provided at the top of the evaporator like a falling film evaporator. The liquid is distributed over the evaporator tubes, but vapor flows to the top in counterflow to the liquid. In some embodiments, the process can also include a stream of an inert gas, for example, to enhance entrainment. This gas can be introduced in the lower portion of the calandria.

A stirrer evaporator is yet another type of evaporator that can be used for water removal from the liquid fraction of the fermentation broth. This apparatus includes an external, jacket-heated vessel equipped with a stirrer. In operation, the liquid fraction is placed in the vessel, optionally in batches. The water is evaporated off by boiling with continuous stirring to a desired concentration. This apparatus can increase its evaporation rate by increasing the heating surface by use of optional immersion heating coils. This type of evaporator is particularly useful when the fermentation is highly viscous.

Finally, the spiral tube evaporator is another type of evaporator that can be used for water removal from the liquid fraction of the fermentation broth. The design includes a heat exchanger equipped with spiral heating tubes and a bottom-mounted centrifugal separator. In operation, the liquid fraction flows a boiling film from top to bottom in parallel flow to the vapor. The expanding vapors produce a shear, or pushing effect on the liquid film. The curvature of the path of flow induces a secondary flow which interferes with the movement along the tube axis. This turbulence improves heat transfer and is particularly useful with viscous liquids. The spiral configuration of the heating tubes usefully provides a large heating surface area to height ratio relative to a non-spiral, straight tube design. This apparatus provides large evaporation ratios allowing single pass operation.

As described above, the use of multiple evaporators of any type described above in double, triple, and multi-effect configurations can increase the efficiency of evaporation. Other methods to improve efficiency of operation include, for example, thermal and mechanical vapor recompression. In some embodiments, any combination of multiple-effect configurations, thermal recompression, and mechanical recompression can be used to increase evaporation efficiency.

Thermal vapor recompression involves recompressing the vapor from a boiling chamber (or separator) to a higher pressure. The saturated steam temperature corresponding to the heating chamber pressure is higher so that vapor can be reused for heating. This is accomplished with a steam jet vapor recompressor which operates on the steam jet pump principle. Briefly, the steam jet principle utilizes the energy of steam to create vacuum and handle process gases. Steam under pressure enters a nozzle and produces a high velocity jet. This jet action creates a vacuum that draws in and entrains gas. The mixture of steam and gas is discharged at atmospheric pressure. A quantity of steam, called motive steam, is used to operate the thermal recompressor. The motive steam is transferred to the next effect or to a condenser. The energy of the excess vapor is approximately that of the motive steam quantity used.

In multiple-effect evaporators equipped with thermal vapor recompressors, the heating medium in the first calandria is the product vapor from one of the associated effects, compressed to a higher temperature level by means of a steam ejector. The heating medium in any subsequent effect is the vapor generated in the previous calandria. Vapor from the final effect is condensed with incoming product, optionally supplemented by cooling water as necessary. All recovered water is readily recycled to a fermentation broth.

Mechanical recompressors utilize all vapor leaving one evaporator. The vapor is recompressed to the pressure of the corresponding heating steam temperature of the evaporator. The operating principle is similar to a heat pump. The energy of the vapor condensate can be optionally used to pre-heat further portions of the liquid fraction of the fermentation broth. The mechanical recompression is supplied by use of a high pressure fans or turbocompressors. These fans operate a high velocity and are suited for large flow rates at vapor compression ratios of about 1:1.2 to about 1:2. Rational speeds can be between about 3,000 to about 18,000 rpm. In some embodiments, when particularly high pressures are useful, multiple stage compressors can be used.

In evaporators with equipped with mechanical vapor recompressors, the heating medium in the first effect is vapor developed in the same effect, compressed to a higher temperature by means of a high-pressure fan. Any excess vapor from the high heat section is optionally condensed or can be utilized in a high concentrator.

As described above there are many possible evaporation types that can be arranged in various energy efficient configurations including multiple effect, thermal vapor recompression, mechanical vapor recompression, or combinations of these. Optimal configurations depend on many factors, including, for example, whether media salts are removed prior to evaporation or via crystallization during the evaporation. For the case where salts are removed prior to evaporation, low cost configurations are useful. Exemplary configurations include a falling film triple effect evaporator system or mechanical vapor recompression system. The case where salts are crystallized during the evaporation is more complex due to the possibility of scaling of the heat exchanger surfaces by precipitation of the salts. An exemplary configuration for this case includes triple effect where the first two effects are falling film evaporators (before the onset of crystallization) and the final stage is a forced circulation evaporative crystallizer, for example.

1,4-BDO purification, in particular, can occur in a series of two distillation columns, although more can be used. A first column is used to separate water and other light components from 1,4-BDO, while a second column is used to distill the 1,4-BDO from any residual heavy components. The distillation columns can be operated under vacuum to reduce the required temperatures and reduce unwanted reactions, product degradation, and color formation. Pressure drop across the columns can be minimized to maintain low temperatures in the bottom reboiler. Residence time in the reboiler can be minimized to also prevent unwanted reactions, product degradation, and color formation, by using, for example, a falling film reboiler.

Those skilled in the art will recognize that various configurations of the enumerated centrifugation, filtration, ion exchange, evaporator crystallizer, evaporator, and distillation apparatus are useful in the purification of a compound of interest, including 1,4-BDO. One exemplary configuration includes, for example, disc stack centrifugation, ultrafiltration, evaporative crystallization, ion exchange, and distillation as shown in the flow scheme diagram of FIG. 16. Thus, in some embodiments, the present invention provides a process of isolating 1,4-BDO from a fermentation broth that includes removing a portion of solids by disc stack centrifugation to provide a liquid fraction, removing a further portion of solids from the liquid fraction by ultrafiltration, removing a portion of salts from the liquid fraction by evaporative crystallization, removing a further portion of salts from the liquid fraction by ion exchange, and distilling 1,4-BDO.

Figure 16:
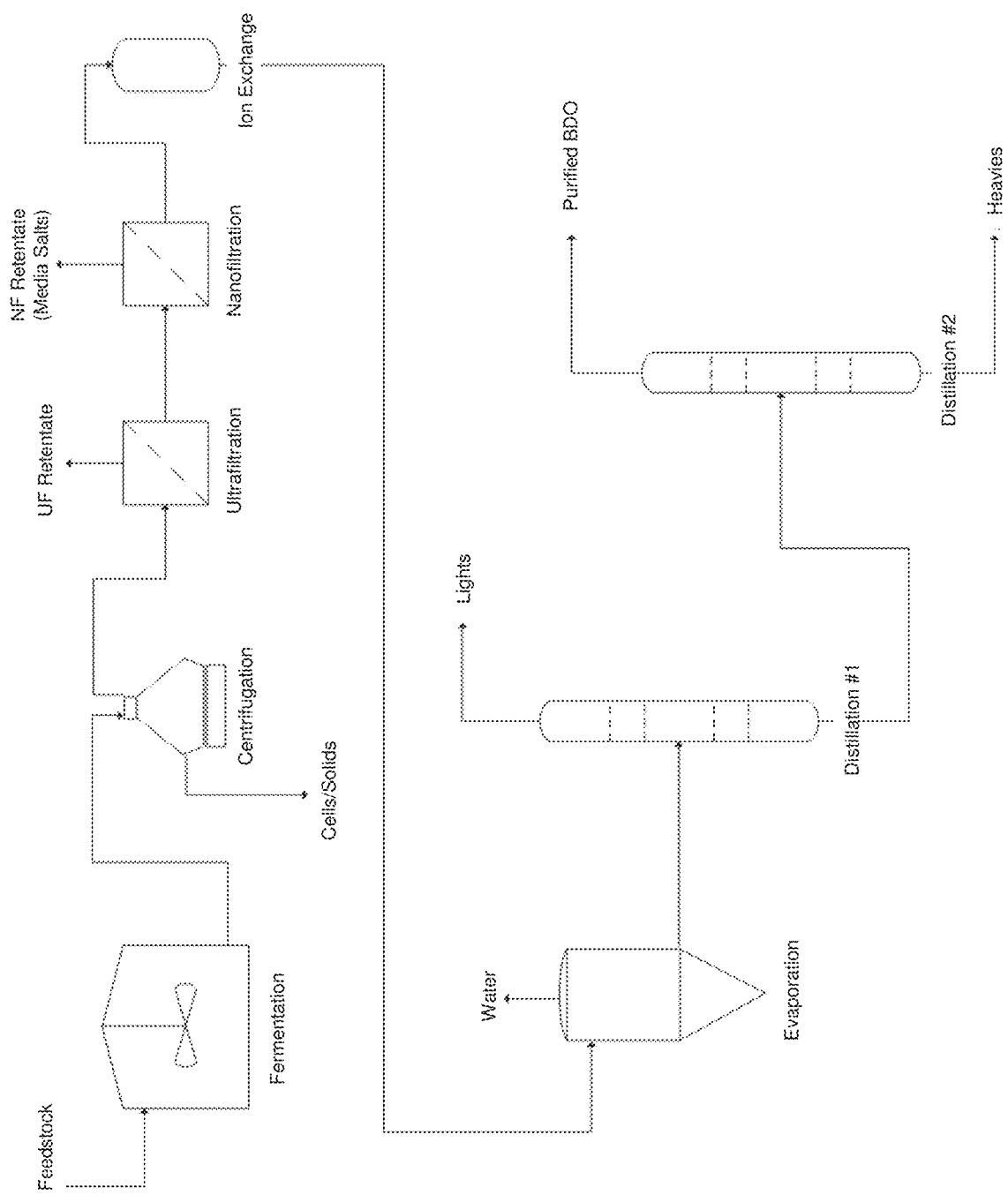
FIG. 16 shows a flow diagram of another complete scheme for the production and isolation of 1,4-BDO.

As shown in FIG. 16, cells and solids are first removed by disc stack centrifugation. The cells can be optionally recycled back into fermentation. Ultrafiltration removes cell debris, DNA, and precipitated proteins. Evaporative crystallization removes a portion of the media salts and water, either of which can be optionally recycled back into fermentation. Following evaporative crystallization, the remaining liquid phase is passed through an ion exchange column to remove further salts. After ion exchange, a portion of the water can be evaporated in an evaporator system, as described above. Distillation of the light fraction, is followed by distillation of 1,4-BDO to provide substantially pure 1,4-BDO.

Another exemplary configuration includes disc stack centrifugation, ultrafiltration, nanofiltration, ion exchange, evaporation, and distillation as shown in FIG. 17. Thus, in some embodiments, the present invention provides a process of isolating 1,4-BDO from a fermentation broth that includes removing a portion of solids by disc stack centrifugation to provide a liquid fraction, removing a further portion of solids from the liquid fraction by ultrafiltration, removing a portion of salts from the liquid fraction by nanofiltration, removing a further portion of salts from the liquid fraction by ion exchange, evaporating a portion of water, and distilling 1,4-BDO.

As shown in FIG. 17, cells and solids are first removed by disc stack centrifugation. The cells can be optionally recycled back into fermentation. Ultrafiltration removes cell debris, DNA, and precipitated proteins. Nanofiltration removes a portion of the media salts, which can be optionally recycled back into fermentation. Following nanofiltration, the permeate is passed through an ion exchange column to remove further salts. After ion exchange, a portion of the water can be evaporated in an evaporator system, as described above. Distillation of the light fraction, is followed by distillation of 1,4-BDO to provide substantially pure 1,4-BDO.

The compound of interest can be any compound for which the product can be engineered for biosynthesis in a microorganism. The processes disclosed herein are applicable to compounds of interest that have boiling points higher than water. Specifically, compounds of interest can have a boiling point between about 120° C. and 400° C. Other properties include high solubility or miscibility in water and the inability to appreciably solubilize salts (when employing evaporative crystallization), and neutral compounds with molecular weights below about 100-150 Daltons (for suitability with nanofiltration).

The processes and principles described herein can be applied to isolate a compound of interest from a fermentation broth, where the compound of interest has the general properties described above. Such a process includes separating a liquid fraction enriched in the compound of interest from a solid fraction that includes the cell mass, followed by water and salt removal, followed by purification.

In some embodiments, the invention also provides a process for recycling components of a fermentation broth. The fermentation broth can include 1,4-BDO or any compound of interest having a boiling point higher than water, cells capable of producing 1,4-BDO or the compound of interest, media salts, and water. The process includes separating a liquid fraction enriched in 1,4-BDO or the compound of interest from a solid fraction that includes the cells. The cells are then recycled into the fermentation broth. Water can be removed before or after separation of salts from the liquid fraction. Evaporated water from the liquid fraction is recycled into the fermentation broth. Salts from the liquid fraction can be removed and recycled into the fermentation broth either by removal of water from the liquid fraction, causing the salts to crystallize, or by nanofiltration and/or ion exchange. The separated salts from nanofiltration are then recycled into the fermentation broth. The process provides 1,4-BDO or other compounds of interest which can be further purified by, for example, by distillation.

In some embodiments, a process for producing a compound of interest, such as 1,4-BDO, includes culturing a compound-producing microorganism in a fermentor for a sufficient period of time to produce the compound of interest. The organism includes a microorganism having a compound pathway comprising one or more exogenous genes encoding a compound pathway enzyme and/or one or more gene disruptions. The process for producing the compound also includes isolating the compound by a process that includes separating a liquid fraction enriched in compound of interest from a solid fraction comprising cells, removing water from the liquid fraction, removing salts from the liquid fraction, and purifying the compound of interest. The compound of interest has a boiling point higher than water.

In a specific embodiment, a process for producing 1,4-BDO includes culturing a 1,4-BDO-producing microorganism in a fermentor for a sufficient period of time to produce 1,4-BDO. The organism includes a microorganism having a 1,4-BDO pathway including one or more exogenous genes encoding a compound pathway enzyme and/or one or more gene disruptions. The process for producing 1,4-BDO also includes isolating the compound by a process that includes separating a liquid fraction enriched in compound of interest from a solid fraction comprising cells, removing water from the liquid fraction, removing salts from the liquid fraction, and purifying the compound of interest.

In particular embodiments where the product of interest is 1,4-BDO, production begins with the culturing of a microbial organism capable of producing 1,4-BDO via a set of 1,4-BDO pathway enzymes. Exemplary microbial organisms include, without limitation, those described in U.S. 2009/0075351 and U.S. 2009/0047719, both of which are incorporated herein by reference in their entirety.

Organisms can be provided that incorporate one or more exogenous nucleic acids that encode enzymes in a 1,4-BDO pathway. Such organisms include, for example, non-naturally occurring microbial organisms engineered to have a complete 1,4-BDO biosynthetic pathway. Such pathways can include enzymes encoded by both endogenous and exogenous nucleic acids. Enzymes not normally present in a microbial host can add in functionality to complete a pathways by including one or more exogenous nucleic acids, for example. One such 1,4-BDO pathway includes enyzmes encoding a 4-hydroxybutanoate dehydrogenase, a succinyl-CoA synthetase, a CoA-dependent succinic semialdehyde dehydrogenase, a 4-hydroxybutyrate:CoA transferase, a 4-butyrate kinase, a phosphotransbutyrylase, an α-ketoglutarate decarboxylase, an aldehyde dehydrogenase, an alcohol dehydrogenase or an aldehyde/alcohol dehydrogenase.

Another pathway can include one or more exogenous nucleic acids encoding a 4-aminobutyrate CoA transferase, a 4-aminobutyryl-CoA hydrolase, a 4-aminobutyrate-CoA ligase, a 4-aminobutyryl-CoA oxidoreductase (deaminating), a 4-aminobutyryl-CoA transaminase, or a 4-hydroxybutyryl-CoA dehydrogenase. Such a pathway can further include a 4-hydroxybutyryl-CoA reductase (alcohol forming), a 4-hydroxybutyryl-CoA reductase, or 1,4-butanediol dehydrogenase Still another pathway can include one or more exogenous nucleic acids encoding a 4-aminobutyrate CoA transferase, a 4-aminobutyryl-CoA hydrolase, a 4-aminobutyrate-CoA ligase, a 4-aminobutyryl-CoA reductase (alcohol forming), a 4-aminobutyryl-CoA reductase, a 4-aminobutan-1-ol dehydrogenase, a 4-aminobutan-1-ol oxidoreductase (deaminating) or a 4-aminobutan-1-ol transaminase. Such a pathway can further include a 1,4-butanediol dehydrogenase.

A further pathway can include one ore more exogenous nucleic acids encoding a 4-aminobutyrate kinase, a 4-aminobutyraldehyde dehydrogenase (phosphorylating), a 4-aminobutan-1-ol dehydrogenase, a 4-aminobutan-1-ol oxidoreductase (deaminating), a 4-aminobutan-1-ol transaminase, a [(4-aminobutanolyl)oxy]phosphonic acid oxidoreductase (deaminating), a [(4-aminobutanolyl)oxy] phosphonic acid transaminase, a 4-hydroxybutyryl-phosphate dehydrogenase, or a 4-hydroxybutyraldehyde dehydrogenase (phosphorylating). Such a pathway can further include a 1,4-butanediol dehydrogenase.

Yet a further pathway can include one or more exogenous nucleic acids encoding an alpha-ketoglutarate 5-kinase, a 2,5-dioxopentanoic semialdehyde dehydrogenase (phosphorylating), a 2,5-dioxopentanoic acid reductase, an alpha-ketoglutarate CoA transferase, an alpha-ketoglutaryl-CoA hydrolase, an alpha-ketoglutaryl-CoA ligase, an alpha-ketoglutaryl-CoA reductase, a 5-hydroxy-2-oxopentanoic acid dehydrogenase, an alpha-ketoglutaryl-CoA reductase (alcohol forming), a 5-hydroxy-2-oxopentanoic acid decarboxylase, or a 5-hydroxy-2-oxopentanoic acid dehydrogenase (decarboxylation). Such a pathway can further include a 4-hydroxybutyryl-CoA reductase (alcohol forming), a 4-hydroxybutyryl-CoA reductase, or a 1,4-butanediol dehydrogenase.

Yet a further pathway can include one or more exogenous nucleic acids encoding a glutamate CoA transferase, a glutamyl-CoA hydrolase, a glutamyl-CoA ligase, a glutamate 5-kinase, a glutamate-5-semialdehyde dehydrogenase (phosphorylating), a glutamyl-CoA reductase, a glutamate-5-semialdehyde reductase, a glutamyl-CoA reductase (alcohol forming), a 2-amino-5-hydroxypentanoic acid oxidoreductase (deaminating), a 2-amino-5-hydroxypentanoic acid transaminase, a 5-hydroxy-2-oxopentanoic acid decarboxylase, or a 5-hydroxy-2-oxopentanoic acid dehydrogenase (decarboxylation). Such a pathway can further include a 4-hydroxybutyryl-CoA reductase (alcohol forming), a 4-hydroxybutyryl-CoA reductase, or a 1,4-butanediol dehydrogenase.

Yet a further pathway can include one or more exogenous nucleic acids encoding a 3-hydroxybutyryl-CoA dehydrogenase, a 3-hydroxybutyryl-CoA dehydratase, a vinylacetyl-CoA Δ-isomerase, or a 4-hydroxybutyryl-CoA dehydratase. Such a pathway can further include a 4-hydroxybutyryl-CoA reductase (alcohol forming), a 4-hydroxybutyryl-CoA reductase, or a 1,4-butanediol dehydrogenase.

Yet a further pathway can include one ore more exogenous nucleic acids encoding a homoserine deaminase, a homoserine CoA transferase, a homoserine-CoA hydrolase, a homoserine-CoA ligase, a homoserine-CoA deaminase, a 4-hydroxybut-2-enoyl-CoA transferase, a 4-hydroxybut-2-enoyl-CoA hydrolase, a 4-hydroxybut-2-enoyl-CoA ligase, a 4-hydroxybut-2-enoate reductase, a 4-hydroxybutyryl-CoA transferase, a 4-hydroxybutyryl-CoA hydrolase, a 4-hydroxybutyryl-CoA ligase, or a 4-hydroxybut-2-enoyl-CoA reductase. Such a pathway can further include a 4-hydroxybutyryl-CoA reductase (alcohol forming), a 4-hydroxybutyryl-CoA reductase, or a 1,4-butanediol dehydrogenase.

Yet a further pathway can include one or more exogenous nucleic acids encoding a succinyl-CoA reductase (alcohol forming), a 4-hydroxybutyryl-CoA hydrolase, a 4-hydroxybutyryl-CoA ligase, or a 4-hydroxybutanal dehydrogenase (phosphorylating). Such a pathway can further include a succinyl-CoA reductase, a 4-hydroxybutyrate dehydrogenase, a 4-hydroxybutyryl-CoA transferase, a 4-hydroxybutyrate kinase, a phosphotrans-4-hydroxybutyrylase, a 4-hydroxybutyryl-CoA reductase, a 4-hydroxybutyryl-CoA reductase (alcohol forming), or a 1,4-butanediol dehydrogenase.

Yet a further pathway can include one or more exogenous nucleic acid encoding a glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, or 4-hydroxybutanal dehydrogenase (phosphorylating). Such a pathway can further include an alpha-ketoglutarate decarboxylase, a 4-hydroxybutyrate dehydrogenase, a 4-hydroxybutyryl-CoA transferase, a 4-hydroxybutyrate kinase, a phosphotrans-4-hydroxybutyrylase, a 4-hydroxybutyryl-CoA reductase, a 4-hydroxybutyryl-CoA reductase (alcohol forming), or a 1,4-butanediol dehydrogenase.

In addition to, or in lieu of, gene insertions, an organism can include gene disruptions to direct the carbon flux toward the direction of synthesizing 1,4-BDO. Such organisms include for example, non-naturally occurring microorganism having a set of metabolic modifications that couple 1,4-butanediol production to growth. In some embodiments, 1,4-butanediol production is not coupled to growth. The set of metabolic modifications can include disruption of one or more genes, or an ortholog thereof. Disruption can include complete gene deletion in some embodiments. Disruption can also include modification via removal of a promoter sequence and the like. For 1,4-BDO production a set of metabolic modifications can include disruption of adhE and ldhA, for example. Other disruption can include the gene mdh. Still other disruptions can include one or more genes selected from the set of genes including mqo, aspA, sfcA, maeB, pntAB, and gdhA. Still other disruptions can include one or more genes selected from the set of genes including pykA, pykF, dhaKLM, deoC, edd, yiaE, ycdW, prpC, and gsk. Still other disruptions can include disruption of pflAB. An exemplary set of disruptions can include one or more genes selected from the set of genes comprising adhE, IdhA, pflAB, mdh, and aspA, including disruption of each of the genes adhE, IdhA, pflAB, mdh, and aspA.

Further exemplary sets of disruptions include adher, nadh6; adher, ppck; adher, sucd4; adher, atps4r; adher, fum; adher, mdh; adher, pfli, ppck; adher, pfli, sucd4; adher, ackr, nadh6; adher, nadh6, pfli; adher, aspt, mdh; adher, nadh6, ppck; adher, ppck, thd2; adher, atps4r, ppck; adher, mdh, thd2; adher, fum, pfli; adher, ppck, sucd4; adher, glcpts, ppck; adher, gludy, mdh; adher, gludy, ppck; adher, fum, ppck; adher, mdh, ppck; adher, fum, gludy; adher, fum, hex1; adher, hex1, pfli; adher, hex1, thd2; adher,frd2, ldh_d, mdh; adher,frd2, ldh_d, me2; adher, mdh, pgl, thd2; adher, g6pdhy, mdh, thd2; adher, pfli, ppck, thd2; adher, ackr, akgd, atps4r; adher, glcpts, pfli, ppck; adher, ackr, atps4r, sucoas; adher, gludy, pfli, ppck; adher, me2, pfli, sucd4; adher, gludy, pfli, sucd4; adher, atps4r, ldh_d, sucd4; adher, fum, hex1, pfli; adher, mdh, nadh6, thd2; adher, atps4r, mdh, nadh6; adher, atps4r, fum, nadh6; adher, aspt, mdh, nadh6; adher, aspt, mdh, thd2; adher, atps4r, glcpts, sucd4; adher, atps4r, gludy, mdh; adher, atps4r, mdh, ppck; adher, atps4r, fum, ppck; adher, aspt, glcpts, mdh; adher, aspt, gludy, mdh; adher, me2, sucd4, thd2; adher, fum, ppck, thd2; adher, mdh, ppck, thd2; adher, gludy, mdh, thd2; adher, hex1, pfli, thd2; adher, atps4r, g6pdhy, mdh; adher, atps4r, mdh, pgl; adher, ackr, frd2, ldh_d; adher, ackr, ldh_d, sucd4; adher, atps4r, fum, gludy; adher, atps4r, fum, hex1; adher, atps4r, mdh, thd2; adher, atps4r, frd2, ldh_d; adher, atps4r, mdh, pgdh; adher, glcpts, ppck, thd2; adher, gludy, ppck, thd2; adher, fum, hex1, thd2; adher, atps4r, me2, thd2; adher, fum, me2, thd2; adher, glcpts, gludy, ppck; adher, me2, pgl, thd2; adher, g6pdhy, me2, thd2; adher, atps4r, frd2, ldh_d, me2; adher, atps4r, frd2, ldh_d, mdh; adher, aspt, ldh_d, mdh, pfli; adher, atps4r, glcpts, nadh6, pfli; adher, atps4r, mdh, nadh6, pgl; adher, atps4r, g6pdhy, mdh, nadh6; adher, ackr, fum, gludy, ldh_d; adher, ackr, gludy, ldh_d, sucd4; adher, atps4r, g6pdhy, mdh, thd2; adher, atps4r, mdh, pgl, thd2; adher, aspt, g6pdhy, mdh, pyk; adher, aspt, mdh, pgl, pyk; adher, aspt, ldh_d, mdh, sucoas; adher, aspt, fum, ldh_d, mdh; adher, aspt, ldh_d, mals, mdh; adher, aspt, icl, ldh_d, mdh; adher,frd2, gludy, ldh_d, ppck, adher, frd2, ldh_d, ppck, thd2; adher, ackr, atps4r, ldh_d, sucd4; adher, ackr, acs, ppc, ppck, adher, gludy, ldh_d, ppc, ppck; adher, ldh_d, ppc, ppck, thd2; adher, aspt, atps4r, glcpts, mdh; adher, g6pdhy, mdh, nadh6, thd2; adher, mdh, nadh6, pgl, thd2; adher, atps4r, g6pdhy, glcpts, mdh; adher, atps4r, glcpts, mdh, pgl; and adher, ackr, ldh_d, mdh, sucd4. The aforementioned genes are included in a broader list of knockout candidates, along with the reactions that these genes catalyze, in Table 1a below.

TABLE 1a

Gene Knockout Candidates in *E. coli*.

| Reaction Abbreviation | Reaction Stoichiometry* | Genes Encoding the Enzyme(s) Catalyzing Each Reaction& |
|---|---|---|
| ACKr | [c]: ac + atp <==> actp + adp | (b3115 or b2296 or b1849) |
| ACS | [c]: ac + atp + coa --> accoa + amp + ppi | b4069 |
| ACt6 | ac[p] + h[p] <==> ac[c] + h[c] | Non-gene associated |
| ADHEr | [c]: etoh + nad <==> acald + h + nadh<br>[c]: acald + coa + nad <==> accoa + h + nadh | (b0356 or b1478 or b1241)<br>(b1241 or b0351) |
| AKGD | [c]: akg + coa + nad --> co2 + nadh + succoa | (b0116 and b0726 and b0727) |
| ASNS2 | [c]: asp-L + atp + nh4 --> amp + asn-L + h + ppi | b3744 |
| ASPT | [c]: asp-L --> fum + nh4 | b4139 |
| ATPS4r | adp[c] + (4) h[p] + pi[c] <==> atp[c] + (3) h[c] + h2o[c] | (((b3736 and b3737 and b3738) and (b3731 and b3732 and b3733 and b3734 and b3735)) or ((b3736 and b3737 and b3738) and (b3731 and b3732 and b3733 and b3734 and b3735) and b3739)) |
| CBMK2 | [c]: atp + co2 + nh4 <==> adp + cbp + (2) h | (b0521 or b0323 or b2874) |
| EDA | [c]: 2ddg6p --> g3p + pyr | b1850 |
| ENO | [c]: 2pg <==> h2o + pep | b2779 |
| FBA | [c]: fdp <==> dhap + g3p | (b2097 or b2925 or b1773) |
| FBP | [c]: fdp + h2o --> f6p + pi | (b4232 or b3925) |
| FDH2 | for[p] + (2) h[c] + q8[c] --> co2[c] + h[p] + q8h2[c]<br>for[p] + (2) h[c] + mqn8[c] --> co2[c] + h[p] + mql8[c] | ((b3892 and b3893 and b3894) or (b1474 and b1475 and b1476)) |
| FRD2 | [c]: fum + mql8 --> mqn8 + succ<br>[c]: 2dmmql8 + fum --> 2dmmq8 + succ | (b4151 and b4152 and b4153 and b4154) |
| FTHFD | [c]: 10fthf + h2o --> for + h + thf | b1232 |
| FUM | [c]: fum + h2o <==> mal-L | (b1612 or b4122 or b1611) |
| G5SD | [c]: glu5p + h + nadph --> glu5sa + nadp + pi | b0243 |
| G6PDHy | [c]: g6p + nadp <==> 6pgl + h + nadph | b1852 |
| GLCpts | glc-D[p] + pep[c] --> g6p[c] + pyr[c] | ((b2417 and b1101 and b2415 and b2416) or (b1817 and b1818 and b1819 and b2415 and b2416) or (b2417 and b1621 and b2415 and b2416)) |
| GLU5K | [c]: atp + glu-L --> adp + glu5p | b0242 |
| GLUDy | [c]: glu-L + h2o + nadp <==> akg + h + nadph + nh4 | b1761 |
| GLYCL | [c]: gly + nad + thf --> co2 + mlthf + nadh + nh4 | (b2904 and b2903 and b2905 and b0116) |
| HEX1 | [c]: atp + glc-D --> adp + g6p + h | b2388 |
| ICL | [c]: icit --> glx + succ | b4015 |
| LDH_D | [c]: lac-D + nad <==> h + nadh + pyr | (b2133 or b1380) |
| MALS | [c]: accoa + glx + h2o --> coa + h + mal-L | (b4014 or b2976) |
| MDH | [c]: mal-L + nad <==> h + nadh + oaa | b3236 |
| ME2 | [c]: mal-L + nadp --> co2 + nadph + pyr | b2463 |
| MTHFC | [c]: h2o + methf <==> 10fthf + h | b0529 |
| NADH12 | [c]: h + mqn8 + nadh --> mql8 + nad<br>[c]: h + nadh + q8 --> nad + q8h2<br>[c]: 2dmmq8 + h + nadh --> 2dmmql8 + nad | b1109 |
| NADH6 | (4) h[c] + nadh[c] + q8[c] --> (3) h[p] + nad[c] + q8h2[c]<br>(4) h[c] + mqn8[c] + nadh[c] --> (3) h[p] + mql8[c] + nad[c]<br>2dmmq8[c] + (4) h[c] + nadh[c] --> 2dmmql8[c] + (3) h[p] + nad[c] | (b2276 and b2277 and b2278 and b2279 and b2280 and b2281 and b2282 and b2283 and b2284 and b2285 and b2286 and b2287 and b2288 ) |

TABLE 1a-continued

Gene Knockout Candidates in E. coli.

| Reaction Abbreviation | Reaction Stoichiometry* | Genes Encoding the Enzyme(s) Catalyzing Each Reaction& |
|---|---|---|
| PFK | [c]: atp + f6p --> adp + fdp + h | (b3916 or b1723) |
| PFLi | [c]: coa + pyr --> accoa + for | (((b0902 and b0903) and b2579) or (b0902 and b0903) or (b0902 and b0903) or (b3951 and b3952)) |
| PGDH | [c]: 6pgc + nadp --> co2 + nadph + ru5p-D | b2029 |
| PGI | [c]: g6p <==> f6p | b4025 |
| PGL | [c]: 6pgl + h2o --> 6pgc + h | b0767 |
| PGM | [c]: 2pg <==> 3pg | (b3612 or b4395 or b0755) |
| PPC | [c]: co2 + h2o + pep --> h + oaa + pi | b3956 |
| PPCK | [c]: atp + oaa --> adp + co2 + pep | b3403 |
| PRO1z | [c]: fad + pro-L --> 1pyr5c + fadh2 + h | b1014 |
| PYK | [c]: adp + h + pep --> atp + pyr | b1854 or b1676) |
| PYRt2 | h[p] + pyr[p] <==> h[c] + pyr[c] | Non-gene associated |
| RPE | [c]: ru5p-D <==> xu5p-D | (b4301 or b3386) |
| SO4t2 | so4[e] <==> so4[p] | (b0241 or b0929 or b1377 or b2215) |
| SUCD4 | [c]: q8 + succ --> fum + q8h2 | (b0721 and b0722 and b0723 and b0724) |
| SUCOAS | [c]: atp + coa + succ <==> adp + pi + succoa | (b0728 and b0729) |
| SULabc | atp[c] + h2o[c] + so4[p] --> adp[c] + h[c] + pi[c] + so4[c] | ((b2422 and b2425 and b2424 and b2423) or (b0763 and b0764 and b0765) or (b2422 and b2424 and b2423 and b3917)) |
| TAL | [c]: g3p + s7p <==> e4p + f6p | (b2464 or b0008) |
| THD2 | (2) h[p] + nadh[c] + nadp[c] --> (2) h[c] + nad[c] + nadph[c] | (b1602 and b1603) |
| THD5 | [c]: nad + nadph --> nadh + nadp | (b3962 or (b1602 and b1603)) |
| TPI | [c]: dhap <==> g3p | b3919 |

The abbreviations for the metabolites in Table 1a are shown below in Table 1b.

TABLE 1b

Metabolite names corresponding to abbreviations used in Table 1a.

| Metabolite Abbreviation | Metabolite Name |
|---|---|
| 10fthf | 10-Formyltetrahydrofolate |
| 1pyr5c | 1-Pyrroline-5-carboxylate |
| 2ddg6p | 2-Dehydro-3-deoxy-D-gluconate 6-phosphate |
| 2dmmq8 | 2-Demethylmenaquinone 8 |
| 2dmmql8 | 2-Demethylmenaquinol 8 |
| 2pg | D-Glycerate 2-phosphate |
| 3pg | 3-Phospho-D-glycerate |
| 6pgc | 6-Phospho-D-gluconate |
| 6pgl | 6-phospho-D-glucono-1,5-lactone |
| ac | Acetate |
| acald | Acetaldehyde |
| accoa | Acetyl-CoA |
| actp | Acetyl phosphate |
| adp | ADP |
| akg | 2-Oxoglutarate |
| amp | AMP |
| asn-L | L-Asparagine |
| asp-L | L-Aspartate |
| atp | ATP |
| cbp | Carbamoyl phosphate |
| co2 | CO2 |
| coa | Coenzyme A |
| dhap | Dihydroxyacetone phosphate |
| e4p | D-Erythrose 4-phosphate |
| etoh | Ethanol |
| f6p | D-Fructose 6-phosphate |
| fad | Flavin adenine dinucleotide oxidized |
| fadh2 | Flavin adenine dinucleotide reduced |
| fdp | D-Fructose 1,6-bisphosphate |
| for | Formate |
| fum | Fumarate |
| g3p | Glyceraldehyde 3-phosphate |
| g6p | D-Glucose 6-phosphate |
| glc-D | D-Glucose |
| glu5p | L-Glutamate 5-phosphate |
| glu5sa | L-Glutamate 5-semialdehyde |
| glu-L | L-Glutamate |
| glx | Glyoxylate |
| gly | Glycine |
| h | H+ |
| h2o | H2O |
| icit | Isocitrate |
| lac-D | D-Lactate |
| mal-L | L-Malate |
| methf | 5,10-Methenyltetrahydrofolate |
| mlthf | 5,10-Methylenetetrahydrofolate |
| mql8 | Menaquinol 8 |
| mqn8 | Menaquinone 8 |
| nad | Nicotinamide adenine dinucleotide |

TABLE 1b-continued

Metabolite names corresponding to abbreviations used in Table 1a.

| Metabolite Abbreviation | Metabolite Name |
|---|---|
| nadh | Nicotinamide adenine dinucleotide - reduced |
| nadp | Nicotinamide adenine dinucleotide phosphate |
| nadph | Nicotinamide adenine dinucleotide phosphate - reduced |
| nh4 | Ammonium |
| oaa | Oxaloacetate |
| pep | Phosphoenolpyruvate |
| pi | Phosphate |
| ppi | Diphosphate |
| pro-L | L-Proline |
| pyr | Pyruvate |
| q8 | Ubiquinone-8 |
| q8h2 | Ubiquinol-8 |
| ru5p-D | D-Ribulose 5-phosphate |
| s7p | Sedoheptulose 7-phosphate |
| so4 | Sulfate |
| succ | Succinate |
| succoa | Succinyl-CoA |
| thf | 5,6,7,8-Tetrahydrofolate |
| xu5p-D | D-Xylulose 5-phosphate |

Any non-naturally occurring microorganism incorporating any combination of the above gene disruptions can also include a gene insertion of at least one exogenous nucleic acid. Any of the gene insertion pathways described above can be integrated with gene disruptions. For example, a pathway including disruptions of the genes adhE, IdhA, pflAB, mdh, and aspA can also include insertion of a 4-hydroxybutanoate dehydrogenase, a CoA-independent succinic semialdehyde dehydrogenase, a succinyl-CoA synthetase, a CoA-dependent succinic semialdehyde dehydrogenase, a 4-hydroxybutyrate:CoA transferase, a glutamate:succinic semialdehyde transaminase, a glutamate decarboxylase, a CoA-independent aldehyde dehydrogenase, a CoA-dependent aldehyde dehydrogenase or an alcohol dehydrogenase. Table 2 below summarizes exemplary engineered organisms for the production of 1,4-BDO that incorporate combinations of gene disruption and gene insertion. Note that gene insertion can be in the form of chromosomal insertion or providing a plasmid.

TABLE 2

Combination Disruption-Insertion Designs for 1,4-BDO Production

| Strain # | Host chromosome | Host Description | Plasmid-based |
|---|---|---|---|
| 1 | ΔldhA | Single deletion derivative of E. coli MG1655 | E. coli sucCD, P. gingivalis sucD, P. gingivalis 4hbd, P. gingivalis Cat2, C. acetobutylicum AdhE2 |
| 2 | ΔadhE ΔldhA ΔpflB | Succinate producing strain; derivative of E. coli MG1655 | E. coli sucCD, P. gingivalis sucD, P. gingivalis 4hbd, P. gingivalis Cat2, C. acetobutylicum AdhE2 |
| 3 | ΔadhE ΔldhA ΔpflB ΔlpdA::K.p.lpdA322 | Improvement of lpdA to increase pyruvate dehydrogenase flux | E. coli sucCD, P. gingivalis sucD, P. gingivalis 4hbd, P. gingivalis Cat2, C. acetobutylicum AdhE2 |
| 4 | ΔadhE ΔldhA ΔpflB ΔlpdA::K.p.lpdA322 | | E. coli sucCD, P. gingivalis sucD, P. gingivalis 4hbd, C. acetobutylicum buk1, C. acetobutylicum ptb, C. acetobutylicum AdhE2 |
| 5 | ΔadhE ΔldhA ΔpflB ΔlpdA::K.p.lpdA322 Δmdh ΔarcA | Deletions in mdh and arcA to direct flux through oxidative TCA cycle | E. coli sucCD, P. gingivalis sucD, P. gingivalis 4hbd, P. gingivalis Cat2, C. acetobutylicum AdhE2 |
| 6 | ΔadhE ΔldhA ΔpflB ΔlpdA::K.p.lpdA322 Δmdh ΔarcA | | M. bovis sucA, E. coli sucCD, P. gingivalis sucD, P. gingivalis 4hbd, P. gingivalis Cat2, C. acetobutylicum AdhE2 |
| 7 | ΔadhE ΔldhA ΔpflB ΔlpdA::K.p.lpdA322 Δmdh ΔarcA gltAR163L | Mutation in citrate synthase to improve anaerobic activity | E. coli sucCD, P. gingivalis sucD, P. gingivalis 4hbd, P. gingivalis Cat2, C. acetobutylicum AdhE2 |
| 8 | ΔadhE ΔldhA ΔpflB ΔlpdA::K.p.lpdA322 Δmdh ΔarcA gltAR163L | | M. bovis sucA, E. coli sucCD, P. gingivalis sucD, P. gingivalis 4hbd, P. gingivalis Cat2, C. acetobutylicum AdhE2 |
| 9 | ΔadhE ΔldhA ΔpflB ΔlpdA::K.p.lpdA322 Δmdh ΔarcA gltAR163L | | M. bovis sucA, E. coli sucCD, P. gingivalis sucD, P. gingivalis 4hbd, P. gingivalis Cat2, C. beijerinckii Ald |
| 10 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd | Succinate branch of upstream pathway integrated into ECKh-422 | P. gingivalis Cat2, C. beijerinckii Ald |
| 11 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd | Succinate and alpha-ketoglutarate upstream pathway branches integrated into ECKh-422 | P. gingivalis Cat2, C. beijerinckii Ald |
| 12 | ΔadhE ΔldhA ΔpflB ΔlpdA::K.p.lpdA322 Δmdh ΔarcA gltAR163L fimD:: E. coli sucCD, | | C. acetobutylicum buk1, C. acetobutylicum ptb, |

TABLE 2-continued

Combination Disruption-Insertion Designs for 1,4-BDO Production

| Strain # | Host chromosome | Host Description | Plasmid-based |
|---|---|---|---|
| | P. gingivalis sucD, P. gingivalis 4hbd fimD:: M. bovis sucA, C. kluyveri 4hbd | | C. beijerinckii Ald |
| 13 | ΔadhE ΔldhA ΔpflB ΔlpdA::K.p.lpdA322 Δmdh ΔarcA gltAR163L ΔackA fimD:: E. coli sucCD, P. gingivalis sucD, P. gingivalis 4hbd fimD:: M. bovis sucA, C. kluyveri 4hbd | Acetate kinase deletion of ECKh-432 | P. gingivalis Cat2, C. beijerinckii Ald |
| 14 | ΔadhE ΔldhA ΔpflB ΔlpdA::K.p.lpdA322 Δmdh ΔarcA gltAR163L ΔackA Δppc::H.i.ppck fimD:: E. coli sucCD, P. gingivalis sucD, P. gingivalis 4hbd fimD:: M. bovis sucA, C. kluyveri 4hbd | Acetate kinase deletion and PPC/PEPCK replacement of ECKh-432 | P. gingivalis Cat2, C. beijerinckii Ald |
| 15 | ΔadhE ΔldhA ΔpflB ΔlpdA::fnr-pflB6-K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd | Replacement of lpdA promoter with anaerobic promoter in ECKh-432 | P. gingivalis Cat2, C. beijerinckii Ald |
| 16 | ΔadhE ΔldhA ΔpflB ΔlpdA:: K.p.lpdA322 ΔpdhR:: fnr-pflB6 Δmdh ΔarcA gltAR163L fimD:: E. coli sucCD, P. gingivalis sucD, P. gingivalis 4hbd fimD:: M. bovis sucA, C. kluyveri 4hbd | Replacement of pdhR and aceEF promoter with anaerobic promoter in ECKh-432 | P. gingivalis Cat2, C. beijerinckii Ald |
| 17 | ΔadhE ΔldhA ΔpflB ΔlpdA:: K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd fimD:: C. acetobutylicum buk1, C. acetobutylicum ptb | Integration of BK/PTB into ECKh-432 | C. beijerinckii Ald |
| 18 | ΔadhE ΔldhA ΔpflB ΔlpdA:: K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd fimD:: C. acetobutylicum buk1, C. acetobutylicum ptb | | C. beijerinckii Ald, G. thermoglucosidasius adh1 |
| 19 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd rrnC::cscAKB | Non-PTS sucrose genes inserted into ECKh-432 | P. gingivalis Cat2, C. beijerinckii Ald |
| 20 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd rrnC::cscAKB | | C. acetobutylicum buk1, C. acetobutylicum ptb, C. beijerinckii Ald |

*The delta symbol (Δ) indicates gene deletion.

The strains summarized in Table 2 are as follows: Strain 1: Single deletion derivative of E. coli MG1655, with deletion of endogenous ldhA; plasmid expression of E. coli sucCD, P. gingivalis sucD, P. gingivalis 4hbd, P. gingivalis Cat2, C. acetobutylicum AdhE2. Strain 2: Host strain AB3, a succinate producing strain, derivative of E. coli MG1655, with deletions of endogenous adhE ldhA pflB; plasmid expression of E. coli sucCD, P. gingivalis sucD, P. gingivalis 4hbd, P. gingivalis Cat2, C. acetobutylicum AdhE2.

Strain 3: Host strain ECKh-138, deletion of endogenous adhE, ldhA, pflB, deletion of endogenous 1pdA and chromosomal insertion of Klebsiella pneumoniae 1pdA with a Glu354Lys mutation at the 1pdA locus; plasmid expression of E. coli sucCD, P. gingivalis sucD, P. gingivalis 4hbd, P. gingivalis Cat2, C. acetobutylicum AdhE2; strain provides improvement of 1pdA to increase pyruvate dehydrogenase flux. Strain 4: Host strain ECKh-138, deletion of endogenous adhE, ldhA, pflB, and 1pdA, chromosomal insertion of Klebsiella pneumoniae 1pdA with a Glu354Lys mutation; plasmid expression E. coli sucCD, P. gingivalis sucD, P. gingivalis 4hbd, C. acetobutylicum buk1, C. acetobutylicum ptb, C. acetobutylicum AdhE2.

Strain 5: Host strain ECKh-401, deletion of endogenous adhE, IdhA, pflB, deletion of endogenous lpdA and chromosomal insertion of Klebsiella pneumoniae lpdA with a Glu354Lys mutation at the lpdA locus, deletion of endogenous mdh and arcA; plasmid expression of E. coli sucCD, P. gingivalis sucD, P. gingivalis 4hbd, P. gingivalis Cat2, C. acetobutylicum AdhE2; strain has deletions in mdh and arcA to direct flux through oxidative TCA cycle. Strain 6: host strain ECKh-401, deletion of endogenous adhE, IdhA, pflB, deletion of endogenous lpdA and chromosomal insertion of Klebsiella pneumoniae lpdA with a Glu354Lys mutation at the lpdA locus, deletion of endogenous mdh and arcA; plasmid expression of M. bovis sucA, E. coli sucCD, P. gingivalis sucD, P. gingivalis 4hbd, P. gingivalis Cat2, C. acetobutylicum AdhE2.

Strain 7: Host strain ECKh-422, deletion of endogenous adhE, IdhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant; plasmid expression of E. coli sucCD, P. gingivalis sucD, P. gingivalis 4hbd, P. gingivalis Cat2, C. acetobutylicum AdhE2; strain has mutation in citrate synthase to improve anaerobic activity. Strain 8: strain ECKh-422, deletion of endogenous adhE, IdhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant; plasmid expression of M. bovis sucA, E. coli sucCD, P. gingivalis sucD, P. gingivalis 4hbd, P. gingivalis Cat2, C. acetobutylicum AdhE2. Strain 9: host strain ECKh-422, deletion of endogenous adhE, IdhA, pflB, deletion of endogenous lpdA and chromosomal insertion of Klebsiella pneu-

*moniae* lpdA with a Glu354Lys mutation at the lpdA locus, deletion of endogenous mdh and arcA, chromosomal replacement of gltA with gltA Arg163Leu mutant; plasmid expression of *M. bovis* sucA, *E. coli* sucCD, *P. gingivalis* sucD, *P. gingivalis* 4hbd, *P. gingivalis* Cat2, *C. beijerinckii* Ald.

Strain 10: host strain ECKh-426, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd; plasmid expression of *P. gingivalis* Cat2, *C. beijerinckii* Ald; strain has succinate branch of upstream pathway integrated into strain ECKh-422 at the fimD locus. Strain 11: host strain ECKh-432, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has succinate and alpha-ketoglutarate upstream pathway branches integrated into ECKh-422. Strain 12: host strain ECKh-432, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *C. acetobutylicum* buk1, *C. acetobutylicum* ptb, *C. beijerinckii* Ald.

Strain 13: host strain ECKh-439, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, deletion of endogenous ackA, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has acetate kinase deletion in strain ECKh-432. Strain 14: host strain ECKh-453, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, deletion of endogenous ackA, deletion of endogenous ppc and insertion of *Haemophilus influenza* ppck at the ppc locus, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has acetate kinase deletion and PPC/PEPCK replacement in strain ECKh-432.

Strain 15: host strain ECKh-456, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, replacement of lpdA promoter with fnr binding site, pflB-p6 promoter and RBS of pflB; plasmid expression of *P. gingivalis* Cat2, *C. beijerinckii* Ald; strain has replacement of lpdA promoter with anaerobic promoter in strain ECKh-432. Strain 16: host strain ECKh-455, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbdI, replacement of pdhR and aceEF promoter with fnr binding site, pflB-p6 promoter and RBS of pflB; plasmid expression of *P. gingivalis* Cat2, *C. beijerinckii* Ald; strain has replacement of pdhR and aceEF promoter with anaerobic promoter in ECKh-432.

Strain 17: host strain ECKh-459, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, chromosomal insertion at the fimD locus of *C. acetobutylicum* buk1, *C. acetobutylicum* ptb; plasmid expression of *C. beijerinckii* Ald; strain has integration of BK/PTB into strain ECKh-432. Strain 18: host strain ECKh-459, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, chromosomal insertion at the fimD locus of *C. acetobutylicum* buk1, *C. acetobutylicum* ptb; plasmid expression of *C. beijerinckii* Ald, *G. thermoglucosidasius* adh1.

Strain 19: host strain ECKh-463, deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, insertion at the rrnC locus of non-PTS sucrose operon genes sucrose permease (cscB), D-fructokinase (cscK), sucrose hydrolase (cscA), and a LacI-related sucrose-specific repressor (cscR); plasmid expression of *P. gingivalis* Cat2, *C. beijerinckii* Ald; strain has non-PTS sucrose genes inserted into strain ECKh-432. Strain 20: host strain ECKh-463 deletion of endogenous adhE, IdhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, insertion at the rrnC locus of non-PTS sucrose operon; plasmid expression of *C. acetobutylicum* buk1, *C. acetobutylicum* ptb, *C. beijerinckii* Ald.

Strains engineered for the utilization of sucrose via a phosphotransferase (PTS) system produce significant amounts of pyruvate as a byproduct. Therefore, the use of a non-PTS sucrose system can be used to decrease pyruvate formation because the import of sucrose would not be accompanied by the conversion of phosphoenolpyruvate (PEP) to pyruvate. This will increase the PEP pool and the flux to oxaloacetate through PPC or PEPCK.

Insertion of a non-PTS sucrose operon into the rrnC region can be performed. To generate a PCR product containing the non-PTS sucrose genes flanked by regions of homology to the rrnC region, two oligos are used to PCR amplify the csc genes from Mach1™ (Invitrogen, Carlsbad, Calif.). This strain is a descendent of W strain which is an *E. coli* strain known to be able to catabolize sucrose (Orencio-Trejo et al., Biotechnology Biofuels 1:8 (2008)). The sequence was derived from *E. coli* W strain K011 (accession AY314757) (Shukla et al., *Biotechnol. Lett.* 26:689-693 (2004)) and includes genes encoding a sucrose permease (cscB), D-fructokinase (cscK), sucrose hydrolase (cscA), and a LacI-related sucrose-specific repressor (cscR). The first 53 amino acids of cscR was effectively removed by the placement of the primer. After purification, the PCR product is electroporated into MG1655 electrocompetent cells which had been transformed with pRedET (tet) and prepared according to the manufacturer's instructions (www.genebridges.com/gb/pdf/K001%20Q20E %20BAC %20Modification %20Kit-version2.6-2007-screen.pdf). The PCR product is designed so that it integrates into the genome into the rrnC region of the chromosome. It effectively deletes 191 nucleotides upstream of rrlC (23 S rRNA), all of the rrlC rRNA gene and 3 nucleotides downstream of rrlC and replaces it with the sucrose operon. The entire rrnC::crcAKB region is transferred into the BDO host strain ECKh-432 by P1 transduction (Sambrook et al., Molecular Cloning: A Laboratory Manual, Third Ed., Cold Spring Harbor Laboratory, New York (2001), resulting in ECKh-463 (ΔadhE ΔldhA ΔpflB ΔlpdA::K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd rrnC::cscAKB). Recombinants are selected by growth on sucrose and verified by diagnostic PCR.

Prior to culturing the compound-producing or 1,4-BDO-producing organisms, the raw materials feedstock such as sucrose syrup and media components can be treated, for example, by heat sterilization prior to addition to the production bioreactor to eliminate any biological contaminants. In accordance with some embodiments, the feedstock can include, for example, sucrose or glucose for the fermentation of BDO. In some embodiments, the feedstock can include syngas. Additional media components used to support growth of the microorganisms include, for example, salts, nitrogen sources, buffers, trace metals, and a base for pH control. The major components of an exemplary media package, expressed in g/L of fermentation broth, are shown below in Table 3.

TABLE 3

| Category | Concentration |
| --- | --- |
| N-Source | 3 g/L |
| Buffer | 5 g/L |

TABLE 3-continued

| Category | Concentration |
| --- | --- |
| Salts | 0.65 g/L |
| Base | 1.4 g/L |
| | 10.1 g/L |

The type of carbon source can vary considerably and can include glucose, fructose, lactose, sucrose, maltodextrins, starch, inulin, glycerol, vegetable oils such as soybean oil, hydrocarbons, alcohols such as methanol and ethanol, organic acids such as acetate, syngas, and similar combinations of CO, $CO_2$, and $H_2$. The term "glucose" includes glucose syrups, i.e. glucose compositions comprising glucose oligomers. Plant and plant-derived biomass material can be a source of low cost feedstock. Such feedstock can include, for example, corn, soybeans, cotton, flaxseed, rapeseed, sugar cane and palm oil. Biomass can undergo enzyme or chemical mediated hydrolysis to liberate substrates which can be further processed via biocatalysis to produce chemical products of interest. These substrates include mixtures of carbohydrates, as well as aromatic compounds and other products that are collectively derived from the cellulosic, hemicellulosic, and lignin portions of the biomass. The carbohydrates generated from the biomass are a rich mixture of 5 and 6 carbon sugars that include, for example, sucrose, glucose, xylose, arabinose, galactose, mannose, and fructose.

The carbon source can be added to the culture as a solid, liquid, or gas. The carbon source can be added in a controlled manner to avoid stress on the cells due to overfeeding. In this respect, fed-batch and continuous culturing are useful culturing modes as further discussed below.

The type of nitrogen source can vary considerably and can include urea, ammonium hydroxide, ammonium salts, such as ammonium sulphate, ammonium phosphate, ammonium chloride and ammonium nitrate, other nitrates, amino acids such as glutamate and lysine, yeast extract, yeast autolysates, yeast nitrogen base, protein hydrolysates (including, but not limited to, peptones, casein hydrolysates such as tryptone and casamino acids), soybean meal, Hy-Soy, tryptic soy broth, cotton seed meal, malt extract, corn steep liquor and molasses.

The pH of the culture can be controlled by the addition of acid or alkali. Because pH can drop during culture, alkali can be added as necessary. Examples of suitable alkalis include NaOH and $NH_4OH$.

Exemplary cell growth procedures used in the production of a compound of interest, such as 1,4-BDO, include, batch fermentation, fed-batch fermentation with batch separation; fed-batch fermentation with continuous separation, and continuous fermentation with continuous separation. All of these processes are well known in the art. Depending on the organism design, the fermentations can be carried out under aerobic or anaerobic conditions. In some embodiments, the temperature of the cultures kept between about 30 and about 45° C., including 31, 32, 33, 34, 35, 36, 37, 38, 39, 40, 41, 42, 43, and 44° C.

In batch fermentation, a tank fermenter (or bioreactor) is filled with the prepared media to support growth. The temperature and pH for microbial fermentation is properly adjusted, and any additional supplements are added. An inoculum of a 1,4-BDO-producing organism is added to the fermenter. In batch fermentation the fermentation will generally run for a fixed period and then the products from the fermentation are isolated. The process can be repeated in batch runs.

In fed-batch fermentation fresh media is continuously or periodically added to the fermentation bioreactor. Fixed-volume fed-batch fermentation is a type of fed-batch fermentation in which a carbon source is fed without diluting the culture. The culture volume can also be maintained nearly constant by feeding the growth carbon source as a concentrated liquid or gas. In another type of fixed-volume fed-batch culture, sometimes called a cyclic fed-batch culture, a portion of the culture is periodically withdrawn and used as the starting point for a further fed-batch process. Once the fermentation reaches a certain stage, the culture is removed and the biomass is diluted to the original volume with sterile water or medium containing the carbon feed substrate. The dilution decreases the biomass concentration and results in an increase in the specific growth rate. Subsequently, as feeding continues, the growth rate will decline gradually as biomass increases and approaches the maximum sustainable in the vessel once more, at which point the culture can be diluted again. Alternatively, a fed-batch fermentation can be variable volume. In variable-volume mode the volume of the fermentation broth changes with the fermentation time as nutrient and media are continually added to the culture without removal of a portion of the fermentation broth.

In a continuous fermentation, fresh media is generally continually added with continuous separation of spent medium, which can include the product of interest, such as 1,4-BDO, when the product is secreted. One feature of the continuous culture is that a time-independent steady-state can be obtained which enables one to determine the relations between microbial behavior and the environmental conditions. Achieving this steady-state is accomplished by means of a chemostat, or similar bioreactor. A chemostat allows for the continual addition of fresh medium while culture liquid is continuously removed to keep the culture volume constant. By altering the rate at which medium is added to the chemostat, the growth rate of the microorganism can be controlled.

The continuous and/or near-continuous production of a compound of interesting, such as 1,4-BDO can include culturing a compound-producing organism in sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, organisms that produce a compound of interest can be cultured for hours, if suitable for a particular application. It is to be understood that the continuous and/or near-continuous culture conditions also can include all time intervals in between these exemplary periods. It is further understood that the time of culturing the compound-producing microbial organism is for a sufficient period of time to produce a sufficient amount of product for a desired purpose.

In some embodiments, the culture can be conducted under aerobic conditions. An oxygen feed to the culture can be controlled. Oxygen can be supplied as air, enriched oxygen, pure oxygen or any combination thereof. Methods of monitoring oxygen concentration are known in the art. Oxygen can be delivered at a certain feed rate or can be delivered on demand by measuring the dissolved oxygen content of the culture and feeding accordingly with the intention of maintaining a constant dissolved oxygen content. In other embodiments, the culture can be conducted under substantially anaerobic conditions. Substantially anaerobic means that the amount of oxygen is less than about 10% of saturation for dissolved oxygen in liquid media. Anaerobic conditions include sealed chambers of liquid or solid medium maintained with an atmosphere of less than about 1% oxygen.

Fermentations can be performed under anaerobic conditions. For example, the culture can be rendered substantially free of oxygen by first sparging the medium with nitrogen and then sealing culture vessel (e.g., flasks can be sealed with a septum and crimp-cap). Microaerobic conditions also can be utilized by providing a small hole for limited aeration. On a commercial scale, microaerobic conditions are achieved by sparging a fermentor with air or oxygen as in the aerobic case, but at a much lower rate and with tightly controlled agitation.

In some embodiments, the compound of interest, including 1,4-BDO, can be produced in an anaerobic batch fermentation using genetically modified *E. Coli*. In fermentation, a portion of the feedstock substrate is used for cell growth and additional substrate is converted to other fermentation byproducts. Media components such as salts, buffer, nitrogen, etc can be added in excess to the fermentation to support cell growth. The fermentation broth is thus a complex mixture of water, the compound of interest, byproducts, residual media, residual substrate, and feedstock/media impurities. It is from this fermentation broth that the compound of interest is isolated and purified. An exemplary fermentation broth composition is shown below in Table 4.

TABLE 4*

| Quantity | Component |
|---|---|
| ~100 g/L | 1,4-BDO |
| ~5 g/L | cell mass |
| ~10 g/L | byproducts (ethanol, acetic acid, 4-hydroxybutyric acid, GBL, proteins) |
| <10 g/L | residual media/salts |
| <1 g/L | residual sucrose/glucose |
| <2 g/L | "unfermentables" (feedstock/impurities) |

*Balance water

A product concentration of about 5-15% by weight of 1,4-BDO can be achieved through fermentation based biosynthetic production processes.

It is understood that modifications which do not substantially affect the activity of the various embodiments of this invention are also included within the definition of the invention provided herein. Accordingly, the following examples are intended to illustrate but not limit the present invention.

EXAMPLE I

Centrifugation of Fermentation Broth

This example shows the use of a disc-stack centrifuge to remove cell mass and other solids from a fermentation broth.

1,4-Butanediol fermentation broth produced by a genetically modified *E. coli* was clarified via centrifugation. A GEA-Westfalia disc stack centrifuge was used for this step. The lab-scale centrifuge, model CTC 1 Whispefuge, has a bowl capacity of 1.0 liters and a solids holding space of 0.55 liters. The bowl hood, distributor, disc stacks, and all process wetted parts are constructed with high tensile strength stainless steel. The feed to centrifuge unit was controlled using a peristaltic pump, with the flow rate held constant at approximately 0.25 liters per minute. A back pressure of about 15 psi was maintained in the system by throttling a regulating valve on the outlet centrate flow. The centrifuge was operated at 12,000 rpm and the feed was at ambient room temperature. The centrifugation removes cellular biomass and insoluble materials from the fermentation broth. The concentration of cellular biomass and insoluble material is indicated by the turbidity, as measured by optical density (OD) at 600 nm. The turbidity data for feed fermentation broth and clarified centrate is shown in Table 5. The feed was visibly hazy and had a measured OD of 13.3. The clarified centrate was visually much clearer and had a measured OD of 0.18. Overall the turbidity was decreased by approximately 99%, showing excellent clarification by the disc stack centrifuge.

TABLE 5

Turbidity measured by optical density (OD) at 600 nm

|  | OD at 600 nm |
|---|---|
| Feed, Fermentation Broth | 13.3 |
| Clarified Centrate | 0.18 |

EXAMPLE II

Ultrafiltration of Fermentation Broth

This example shows the ultrafiltration of the fermentation broth following removal of cell mass and other solids by centrifugation conducted in Example I.

A GEA lab scale filtration unit, Model L, was used to further clarify the product produced in Example 1. The Model L filtration unit was equipped with Hydranautics 5K PES flat sheet membranes. Total installed membrane area was 0.144 m$^2$. The transmembrane pressure was maintained at approximately 36 psi by adjusting inlet flow and back pressure regulating valve. The temperature of the feed was maintained at approximately 27° C. using an inlet heat exchanger. The permeate flow rate was measured throughout the course of the experiment to determine the flux. Table 6 shows the permeate flux in liters/m$^2$/h as a function of the volumetric concentration factor (VCF).

TABLE 6

Ultrafiltration flux versus VCF

| VCF | Flux liters/m$^2$/h |
|---|---|
| 1.18 | 15.02 |
| 1.44 | 15.37 |
| 1.86 | 15.29 |
| 2.60 | 15.34 |
| 4.33 | 15.06 |
| 6.50 | 14.79 |

Samples were also drawn throughout the experiment to determine the permeate quality. Protein concentration in the feed and permeate was measured using Bradford Assay. Table 7 shows the protein concentration in the feed, permeate and retentate. The protein concentration decreased by approximately 68% in the permeate compared to the feed.

TABLE 7

Protein concentration measured using Bradford Assay

|  | Protein Concentration, mg/L |
|---|---|
| Feed, Centrifuged Broth | 84.09 |
| UF Permeate | 27.11 |
| UF Retentate | 248.90 |

EXAMPLE III

Nanofiltration of Fermentation Broth

This example shows the nanofiltration of the fermentation broth following ultrafiltration conducted in Example II.

A GEA lab scale filtration unit, Model L, was equipped with GE DK nanofiltration flat sheet membranes. Total installed membrane area was 0.072 m$^2$. This set up was used to filter the UF permeate obtained from Example 2. The transmembrane pressure was maintained at approximately 270 psi by adjusting inlet flow and back pressure regulating valve. The temperature of the feed was maintained at 38° C. using an inlet heat exchanger. The permeate flow was measured throughout the course of the experiment to determine the flux. Table 8 shows the flux in liters/m$^2$/h as a function of the volumetric concentration factor (VCF).

TABLE 8

Nanofiltration flux

| VCF | Flux liters/m2/h |
|---|---|
| 1.33 | 14.69 |
| 1.74 | 13.41 |
| 2.50 | 10.42 |

Samples were also drawn throughout the experiment to determine the permeate quality. Organic acids where measured using LC-MS, salt ions where analyzed using Chromatography (IC), and glucose was measured using an Analox G6 analyzer. Table 9 shows the percent rejection for glucose, ions, and organic acids. At the pH of the feed it is expected that the organic acids are present in their salt form. The nanofiltration permeate also had a visual reduction in color from a distinct yellow in the feed to a very faint yellow in the permeate product.

TABLE 9

Percent rejection of glucose, ions and organic acids by nanofiltration

| Glucose | Monovalent Cations | Divalent Cations | Anions | Organic Acids |
|---|---|---|---|---|
| 88.57% | 72.80% | 100.00% | 82.45% | 64.39% |

EXAMPLE IV

Ion Exchange of Fermentation Broth

This example shows the ion exchange chromatographic purification of the fermentation broth following nanofiltration conducted in Example III.

Nanofiltration permeate obtained from Example III was processed through an ion exchange step to remove the remaining ions and further clarify the product. Amberlite IR 120H, a strong acid cation exchange resin, and Amberlite IRA 67, a weak base anion exchange resin, were used for this step. Individual cation and anion exchange columns, 2 ft high×1 inch diameter, were loaded with $5.3×10^{-3}$ ft$^3$ of cation and anion exchange resins, respectively. The nanofiltration permeate was first fed to cation exchange column, and then to anion exchange column at 10 mL/min and 40° C. The ion exchange was analyzed for ion content via IC. All the remaining ions were removed to a concentration of less than 0.1 mEq/L. All the remaining organic acids were also removed in this step. The product was very clear with no visible yellow color.

EXAMPLE V

Evaporative Crystallization of a Synthetic Feed

This example shows the removal of salts from a synthetic feed by evaporative crystallization on laboratory scale with the aid of a rotary evaporator.

Evaporation was performed using a Buchi Rotavap R-205 at bath temperature of 50° C. and a vacuum of ~100 mm of Hg. A synthetic feed material was prepared with about 8% BDO in water containing approximately 92 mEq/L monovalent cations, 5 mEq/L divalent cations and 125 mEq/L anions. The water was evaporated off from this mixture while the salt ions where simultaneously allowed to precipitate from the solution. Ion concentrations in the solution were monitored throughout the evaporation by taking small sample aliquots for analysis by Ion Chromatography. Prior to analysis the precipitated solids were filtered off. Table 10 shows the concentration of ions in solution (normalized to 100% in the feed sample) as the BDO was concentrated from approximately 10 to 95%. The ion concentrations increased up to the saturation point in the solution (at approximately 30% BDO). After this point further evaporation forced crystallization (precipitation) of the salts. Overall, this evaporative crystallization step caused 97.5% of the salt ions to precipitate from the BDO solution.

TABLE 10

Evaporative precipitation of synthetic broth

| Time, h | BDO wt % | % Monoatomic cations | % Diatomic cations | % Anions |
|---|---|---|---|---|
| 0 | 10.00 | 100.00 | 100.00 | 100.00 |
| 0.25 | 15.74 | 159.75 | 132.32 | 161.25 |
| 0.5 | 33.79 | 344.61 | 159.73 | 353.02 |
| 0.75 | 81.32 | 35.49 | 0.00 | 47.24 |
| 1.5 | 94.25 | 22.43 | 0.00 | 20.17 |

EXAMPLE VI

Salt Solubility

This example shows salt solubility profiles in various small carbon chain diols, including 1,4-BDO.

Salt solubility in different solutions containing varying amounts of 1,4-Butanediol (BDO), 1,3-Propanediol (PDO) or 1,2-Ethanediol (mono etheylene glycol, MEG) was measured. The salts were added to 10 mL of the solution until the solution was saturated. The saturated salt solubility was measured using Ion Chromatography. Table 11 shows salt solubility of four different salts at room temperature (approximately 20° C.). The salt solubility decreases significantly with increases in BDO concentration demonstrating the feasibility of salt removal using evaporative crystallization. Table 12 shows salt solubility of three different salts in different concentrations of 1,4-BDO, PDO or MEG solutions at room temperature. The results show a decrease in salt solubilities going from MEG, to PDO, to 1,4-BDO, demonstrating that 1,4-BDO is best suited for an evaporative crystallization among the three compounds.

TABLE 11

Solubility of four different salts in solutions containing 0 to 100% 1,4-Butanediol (1,4-BDO)

| Solution (% 1,4-BDO) | Average Measured Solubility (wt %) ~20 C. | | | |
|---|---|---|---|---|
| | $KH_2PO_4$ | NaCl | $MgSO_4$ | $(NH_4)_2SO_4$ |
| 0 (Water) | 20.101 | 32.300 | 34.354 | 57.375 |
| 33 | 3.296 | 10.803 | 7.346 | 11.639 |
| 80 | 0.056 | 2.529 | 0.035 | 0.173 |
| 90 | 0.011 | 0.314 | 0.015 | 0.022 |
| 95 | 0.005 | 0.314 | 0.028 | 0.008 |
| 98 | 0.031 | 0.175 | 0.011 | 0.005 |
| 100 | 0.003 | 0.050 | 0.009 | 0.004 |

TABLE 12

Solubility of three different salts in 50, 80 or 100% of 1,4-Butanediol (BDO), 1,3-Propanediol (PDO) or 1,2-Ethanediol (MEG)

| Solvent | Solution (% Solvent) | Average Measured Solubility (wt %) ~20 C. | | |
|---|---|---|---|---|
| | | KCl | $Na_2SO_4$ | $(NH_4)H_2PO_4$ |
| BDO | 50 | 8.21 | 0.63 | 2.97 |
| | 80 | 0.94 | 0.04 | 0.16 |
| | 100 | 0.05 | 0.00 | 0.01 |
| PDO | 50 | 8.70 | 2.38 | 3.62 |
| | 80 | 1.45 | 0.10 | 0.46 |
| | 100 | 0.30 | 0.01 | 0.09 |
| MEG | 50 | 14.11 | 9.42 | 8.06 |
| | 80 | 7.72 | 1.81 | 2.90 |
| | 100 | 4.76 | 0.69 | 1.22 |

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A process of isolating 1,4-butanediol (1,4-BDO) from a fermentation broth, the process consisting of:
    separating a liquid fraction enriched in 1,4-BDO from a solid fraction of the fermentation broth comprising cells in a separation step consisting of filtration, wherein the filtration consists of ultrafiltration, and wherein the fermentation broth comprises 1,4-BDO at a concentration of about 5%-15% by weight of 1,4-BDO;

removing salts from the liquid fraction, wherein removing the salts comprises nanofiltration followed by ion exchange;

removing water from said liquid fraction, and purifying 1,4-BDO from the liquid fraction by distillation after removing salts and water; to produce a 1,4-BDO product at least 98% pure.

2. The process of claim 1, wherein ultrafiltration comprises filtering through a membrane having a pore size from about 0.005 to about 0.1 microns.

3. The process of claim 1, wherein removing water is accomplished by evaporation with an evaporator system comprising one or more effects.

4. The process of claim 3, wherein said evaporator system comprises a double- or triple-effect evaporator.

5. The process of claim 3, wherein said evaporator system further comprises a thermal recompressor.

6. The process of claim 3, wherein said evaporator system further comprises a mechanical recompressor.

7. The process of claim 3, wherein said evaporator system comprises an evaporator selected from the group consisting of a falling film evaporator, a short path falling film evaporator, a forced circulation evaporator, a plate evaporator, a circulation evaporator, a fluidized bed evaporator, a rising film evaporator, a counterflow-trickle evaporator, a stirrer evaporator, and a spiral tube evaporator.

8. The process of claim 3, wherein said evaporator system comprises a vacuum.

9. The process of claim 1, wherein substantially all of the salts are removed prior to removal of water.

10. The process of claim 1, wherein nanofiltration comprises filtering through a membrane having a pore size range from about 0.0005 to about 0.005 microns.

11. The process of claim 1, wherein substantially all of the salts are removed after removal of water.

12. The process of claim 1, wherein the salts are partially removed, followed by removal of substantially all of the water, and then remaining salts are removed.

13. The process of claim 1, wherein removing salts further comprises crystallizing salts.

14. The process of claim 1, wherein removing salts further comprises precipitating salts by water removal.

* * * * *